United States Patent
Wei et al.

(10) Patent No.: US 6,261,801 B1
(45) Date of Patent: Jul. 17, 2001

(54) NUCLEIC ACIDS ENCODING TUMOR NECROSIS FACTOR RECEPTOR 5

(75) Inventors: Ying-Fei Wei, San Mateo, CA (US); Reiner Gentz, Silver Spring, MD (US); Jian Ni, Rockville, MD (US); Steven M. Ruben, Olney, MD (US)

(73) Assignee: Human Genome Sceineces, Inc., Rockville, MD (US)

( * ) Notice: Subject to any disclaimer, the term of this patent is extended or adjusted under 35 U.S.C. 154(b) by 0 days.

(21) Appl. No.: 09/006,353

(22) Filed: Jan. 13, 1998

Related U.S. Application Data

(60) Provisional application No. 60/054,885, filed on Aug. 7, 1997, and provisional application No. 60/035,496, filed on Jan. 14, 1997.

(51) Int. Cl.$^7$ .............................. C12P 21/02; C07H 21/00
(52) U.S. Cl. ................. 435/69.1; 435/320.1; 435/252.3; 435/361; 435/254.2; 435/366; 435/348; 530/350; 536/23.5
(58) Field of Search ................... 536/23.5; 435/320.1, 435/252.3, 69.1; 530/350

(56) References Cited

U.S. PATENT DOCUMENTS 5,580,756 * 12/1996 Linsley et al. ...................... 435/69.7

FOREIGN PATENT DOCUMENTS

| WO 94/01548 | * 1/1994 | (WO) . |
| WO 98/58062 | 12/1998 | (WO) . |
| 99/00423 | 1/1999 | (WO) . |
| WO 99/09165 | 2/1999 | (WO) . |

OTHER PUBLICATIONS

Hillier et al., Generation and analysis of 280,000 human expressed sequence tags, Accession Nos. A A150849 and AA150541, Dec. 1996.*
Hillier, L. et al., Genbank Acc. No. T71406 (Mar. 1995).
Hillier, L. et al., Genbank Acc. No. R10996 (Apr. 1995).
Hillier, L. et al., Genbank Acc. No. R10995 (Apr. 1995).
Hillier, L. et al., Geneseq Acc. No. G23178 (May 1996).
Hillier, L. et al., Genbank Acc. No. T71272 (Mar. 1995).
Pitti, R. M. et al., J. Biol. Chem., 271: 12687–12690 (1996).
Pan, G. et al., Science 277: 815–818 (1997).
Sheridan, J. P. et al., Science 27: 818–821 (1997).
Macfarlane, M. et al., J. Biol. Chem., 272: 25417–25420 (1997).
Schneider, P. et al., FEBS Letters, 416: 329–334 (1997).
GenBank Accession No: AF014794 (Mar. 13, 1998).
GenBank Accession No: AF033854 (Nov. 27, 1997).
GenBank Accession No: AF020502 (Sep. 28, 1997).
GenBank Accession No: AF016267 (Oct. 16, 1997).
GenBank Accession No. AFO12536 (Aug. 21, 1997).
GenBank Accession No: AF012629 (Aug. 21, 1997).
NCBI Entrez, GenBank Report, Accession No. AA031883, From Hiller, et al. (Aug. 21, 1996).

* cited by examiner

Primary Examiner—Lorraine Spector
Assistant Examiner—Eileen B. O'Hara
(74) Attorney, Agent, or Firm—Sterne, Kessler, Goldstein & Fox, P.L.L.C.

(57) ABSTRACT

The present invention relates to a novel human gene encoding a polypeptide which is a member of the TNF receptor family, and has now been found to bind TRAIL. More specifically, an isolated nucleic acid molecule is provided encoding a human polypeptide named tumor necrosis factor receptor-5, sometimes referred to as "TNFR-5" or "TR5", and now referred to hereinafter as "TRAIL receptor without intracellular domain" or "TRID." TRID polypeptides are also provided, as are vectors, host cells, and recombinant methods for producing the same. The invention further relates to screening methods for identifying agonists or antagonists of TRAIL polypeptide activity. Also provided are diagnostic and therapeutic methods utilizing such compositions.

153 Claims, 23 Drawing Sheets

CCTCTCCACGCGCACGAACTCAGCCAACGATTTCTGATAGATTTTTGGGAGTTTGACCAG

AGATGCAAGGGGTGAAGGAGCGCTTCCTACCGTTAGGGAACTCTGGGGACAGAGCGCCCC

GGCCGCCTGATGGCCGAGGCAGGGTGCGACCCAGGACCCAGGACGGCGTCGGGAACCATA

CCATGGCCCGGATCCCCAAGACCCTAAAGTTCGTCGTCGTCATCGTCGCGGTCCTGCTGC
  M  A  R  I  P  K  T  L  K  F  V  V  V  I  V  A  V  L  L  P

CAGTCCTAGCTTACTCTGCCACCACTGCCCGGCAGGAGGAAGTTCCCCAGCAGACAGTGG
  V  L  A  Y  S  A  T  T  A  R  Q  E  E  V  P  Q  Q  T  V  A

CCCCACAGCAACAGAGGCACAGCTTCAAGGGGGAGGAGTGTCCAGCAGGATCTCATAGAT
  P  Q  Q  Q  R  H  S  F  K  G  E  E  C  P  A  G  S  H  R  S

CAGAACATACTGGAGCCTGTAACCCGTGCACAGAGGGTGTGGATTACACCAACGCTTCCA
  E  H  T  G  A  C  N  P  C  T  E  G  V  D  Y  T  N  A  S  N

ACAATGAACCTTCTTGCTTCCCATGTACAGTTTGTAAATCAGATCAAAAACATAAAAGTT
  N  E  P  S  C  F  P  C  T  V  C  K  S  D  Q  K  H  K  S  S

CCTGCACCATGACCAGAGACACAGTGTGTCAGTGTAAAGAAGGCACCTTCCGGAATGAAA
  C  T  M  T  R  D  T  V  C  Q  C  K  E  G  T  F  R  N  E  N

ACTCCCCAGAGATGTGCCGGAAGTGTAGCAGGTGCCCTAGTGGGGAAGTCCAAGTCAGTA
  S  P  E  M  C  R  K  C  S  R  C  P  S  G  E  V  Q  V  S  N

ATTGTACGTCCTGGGATGATATCCAGTGTGTTGAAGAATTTGGTGCCAATGCCACTGTGG
  C  T  S  W  D  D  I  Q  C  V  E  E  F  G  A  N  A  T  V  E

AAACCCCAGCTGCTGAAGAGACAATGAACACCAGCCCGGGGACTCCTGCCCCAGCTGCTG
  T  P  A  A  E  E  T  M  N  T  S  P  G  T  P  A  P  A  A  E

AAGAGACAATGAACACCAGCCCAGGGACTCCTGCCCCAGCTGCTGAAGAGACAATGACCA
  E  T  M  N  T  S  P  G  T  P  A  P  A  A  E  E  T  M  T  T

CCAGCCCGGGGACTCCTGCCCCAGCTGCTGAAGAGACAATGACCACCAGCCCGGGGACTC
  S  P  G  T  P  A  P  A  A  E  E  T  M  T  T  S  P  G  T  P

CTGCCCCAGCTGCTGAAGAGACAATGACCACCAGCCCGGGGACTCCTGCCTCTTCTCATT
  A  P  A  A  E  E  T  M  T  T  S  P  G  T  P  A  S  S  H  Y

FIG.1A

```
ACCTCTCATGCACCATCGTAGGGATCATAGTTCTAATTGTGCTTCTGATTGTGTTTGTTT
  L   S   C   T   I   V   G   I   I   V   L   I   V   L   L   I   V   F   V   *
GAAAGACTTCACTGTGGAAGAAATTCCTTCCTTACCTGAAAGGTTCAGGTAGGCGCTGGC

TGAGGGCGGGGGGCGCTGGACACTCTCTGCCCTGCCTCCCTCTGCTGTGTTCCCACAGAC

AGAAACGCCTGCCCCTGCCCCAAGTCCTGGTGTCTCCAGCCTGGCTCTATCTTCCTCCTT

GTGATCGTCCCATCCCCACATCCCGTGCACCCCCCAGGACCCTGGTCTCATCAGTCCCTC

TCCTGGAGCTGGGGGTCCACACATCTCCCAGCCAAGTCCAAGAGGCAGGGCCAGTTCCTC

CCATCTTCAGGCCCAGCCAGGCAGGGGGCAGTCGGCTCCTCAACTGGGTGACAAGGGTGA

GGATGAGAAGTGGTCACGGGATTTATTCAGCCTTGGTCAGAGCAGAACACAGAGATTTTC

CGTGAAAAAAAA
```

| Start | Name | Sequence |
|---|---|---|
|  | Consensus #1 | . . . . . . . . . . . . . . . . . . . . . . . . . . . . . . . . . . . . . . . . . . . . |
| 198 | TNFR1 | - - G A V H L P Q P V S T R S Q H T Q P T P E P S T A P S T - - V I F F G - L - - - - - |
| 212 | TNFR2 | - - T P P E G S D S T A P S T Q E P E A P P E Q D L I A S T - - - - - L P M G P S P P A |
| 200 | NGFR | - - L A I L L S - - - - - - - - - - - - - - - - - - - - - - - - - - - V A G V - V T T V |
| 224 | LTbR | - - - - - - - - - - - - - - - - - - - - - - - - - - - - - - - - - - - - - - - - - - - |
| 159 | FAS | - - A R S S Q A L S P H P Q P T H L P Y V S E M L E A R - - - - - G W L - - - - - - - |
| 130 | CD27 | - - - - - - - - - - - - - - - - - - - - - - - - - - - - - - - - - - - - - - - - - - - |
| 204 | CD30 | - A A S K L T R A P D S P S S V G R P S S D P G L S P T Q P - - - - - T A G H M Q T L |
| 194 | CD40 | A L V V I P - - - - - - - - - - - - - - - - - - - - - - - - - - - - - - - - - - - - - |
| 164 | 4-1BB | D L S P G A S S V T P P A P A R E P G H S P Q I I S - - - - - C P E G S G D C R |
| 169 | OX40 | - R D P P A T Q P Q E T Q G P P - - - - - - - - - - - - - - - - - - - - - - - - - - - |
| 200 | VC22 | - G L S E S I L T - - - - - - - - - - - - - - - - - S E L T I T M N H T D C N |
| 200 | CRMB | - G L S E S I S T - - - - - - - - - - - - - - - - - S E L T I T M N H K D C D |
| 153 | TNFR-like | - - - - - - - - - - - - - - - - - - - - - - - - - - - - - - - - F G - - - - - - - - |

FIG. 2H

Multiple sequence alignment of TNF receptor family members (transmembrane region). Consensus #1 at top; rows labeled (with starting residue numbers): TNFR1 (252), TNFR2 (236), NGFR (230), LTbR (230), LTβR (178), FAS (164), CD27 (242), CD30 (200), CD40 (190), 4-1BB (184), OX40 (221), VC22 (221), CRMB (221), TNFR-like (155).

| Protein | Start | Sequence (aligned, gaps shown as –) |
|---|---|---|
| TNFR1 | 252 | EGSTGDFAL– – – – – – – – – – – C L L S L L F I G L M Y – – – – – – – – – V |
| TNFR2 | 236 | M G S S Q P V V T – – – – – – – – – P V G L I V G V – – – – – – – – – V |
| NGFR | 230 | – – – – R G T T D N L I P V Y C S I L A A V V G L V A – – – – – – – – – |
| LTbR | 178 | – D F A L – – – – – – – – – – – V L F L F T T V L I P L I V – – – – – – – G |
| FAS | 164 | A D – – – – – – – – – – – – – – – C L L – L L P I P L I V – – – – – – – – |
| CD27 | 242 | K Q C E P D Y Y L D E A G R C T A C V S C S R D D L V E K T P C A W N S S R T C |
| CD30 | 200 | – – – – – – – – – – – – – – – – H F G I L F A I L L V L V F I K K – – – – – |
| CD40 | 190 | – – – – – – – – – – – – – – – – – – – – – – – – – – – – – – – – – – |
| 4-1BB | 184 | – F F L – – – – – – – – – – – – – – – – – – – – – – – – – – – – – – – |
| OX40 | 221 | A R P I T V Q P T E A – – – – – – – – – – – – – – – – – – – – – – – – |
| VC22 | 221 | P V F R E E Y – – – – – – F S V L N K V A T S G F F T G E N R – – – – – |
| CRMB | 221 | P V F R N G Y – – – – – – F S V L N E V A T S G F F T G Q N R – – – – – |
| TNFR-like | 155 | – – – – – – – – – – – – – – – – – – – – – – – – – – – – – – – – – – |

Highlighted (black) consensus blocks mark the predicted transmembrane region (e.g., L L / L L F / L L P / V V in column positions indicated).

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | · | · | · | · | · | · | · | · | · | · | · | · | · | · | · | · | · | · | · | · | · | · | · | · | · | · | · | Consensus #1 |
| 304 | C | P | N | F | A | A | P | R | R | E | V | A | P | P | Y | Q | G | A | D | P | I | L | A | T | A | - | - | TNFR1 |
| 324 | - | - | - | - | - | - | P | S | S | S | S | S | S | L | E | S | S | A | S | A | L | - | - | - | - | - | - | TNFR2 |
| 311 | S | Q | S | L | H | D | Q | Q | P | H | T | Q | T | A | S | G | Q | A | L | K | - | - | - | - | - | - | - | NGFR |
| 288 | - | - | - | - | - | - | P | M | S | G | D | L | S | P | S | P | A | G | P | P | T | - | - | - | - | - | - | LTbR |
| 236 | - | - | - | - | - | - | - | - | - | - | - | - | - | - | - | - | - | - | - | - | - | I | A | G | V | - | - | FAS |
| 171 | A | R | T | L | S | T | H | W | P | P | Q | R | S | L | C | S | S | D | F | I | - | R | I | L | V | I | F | CD27 |
| 361 | S | K | T | L | P | I | P | T | S | A | P | V | A | L | S | S | T | G | K | P | V | L | D | A | G | P | V | CD30 |
| 241 | - | - | - | - | - | - | - | - | - | - | - | D | L | P | G | S | N | T | A | A | P | V | - | - | - | - | - | CD40 |
| 193 | - | - | - | - | - | - | - | - | - | - | - | - | - | - | - | - | A | L | T | S | T | A | L | F | L | - | - | 4-1BB |
| 224 | - | - | - | - | - | - | - | - | - | - | - | - | - | - | - | - | - | V | L | G | L | L | - | - | - | - | - | OX40 |
| 274 | - | - | - | - | - | - | A | K | N | D | D | G | - | M | - | - | - | - | - | - | - | - | - | - | - | - | - | VC22 |
| 276 | - | - | - | - | - | - | T | K | N | D | D | D | S | I | - | - | - | - | - | - | - | - | - | - | - | - | - | CRMB |
| 205 | - | - | - | - | - | - | - | - | - | - | - | - | P | A | P | A | A | A | E | E | T | M | T | T | S | - | - | TNFR-like |

| Pos | Sequence | Protein |
|---|---|---|
|  | ..........QLPTRNPPQKWEDSAHKPQSLDGFDTDDPATLYAVVE | Consensus #1 |
| 329 | --VEKLL--LASDPIPNPLQKWEDSAHKPQSLDTDDPATLYAVVE | TNFR1 |
| 339 | --------DRRAPTRNQP-------------DDPARA--SDSS | TNFR2 |
| 347 | ------------------------------------EA----NGS | NGFR |
| 303 | ---APSLEEVVLQQ-----SPL------------------EAE | LTbR |
| 240 | -MTLS-QV---------------------------------- | FAS |
| 207 | GALFLL-----------------------------QAREL--- | CD27 |
| 401 | SSAFLLCHRRACRKRIRQKLHLCYPVQTSQPKLELVDSRP--- | CD30 |
| 252 | -QETL-----------------------------------HQ | CD40 |
| 216 | GRKKLL------------------------------------ | 4-1BB |
| 245 | ------------------------------------------ | OX40 |
| 281 | -----MSHSETVTLAGDCLSSVDIYILYSNTN---------- | VC22 |
| 284 | -----MPHSESVTLVGDCLSSVDIYILYSNTN---------- | CRMB |
| 217 | PGTPAPAAEETMTTSPGTPAS--------------------- | TNFR-like |

FIG. 2M

```
                                                                            Consensus #1
405  A T W R R T P R R E A T L E L L G R V - L R D M D L L G C - - - - - - - - - - - - -   TNFR1
409  - - - - - D S S P S E S - P K D E - - - - - - Q V P F S K E E C A F - - - - - - - -   TNFR2
388  A S W A T Q D S - - - - - - - - - - - - - - - - - - - - - - - - - - - - - - - - -   NGFR
365  - - - - - - - - - - - - R G P G D P - P A P P - E P P Y P T P E E G A - - - - - - -   LtbR
279  R N W H Q L H G K K E A - Y D T L I K D L K K A N L - C T L A E K I Q - - - - - - -   FAS
239  - - - E E E G S T I - - - - - - - - - - - - - - - - - - - - - - - - - - - - - - -   CD27
481  E S L P L Q D A S P A G G - P S S P R D L P E P R V S T E H T N N K I E K I Y H - -   CD30
263  - - - - - - - - - - - - - - - - - - - - - - - - - - - - - - - - - - - - - - - - -   CD40
222  - - - - - - - - - - - - - - - - - - - - - - - - - - - - - - - - - - - - Y - - - -   4-1BB
260  - - - - - - - - - - - - - - - - - - - - - - - - - - - - - - - - - - - - - - - - -   OX40
339  - - - - - - - - - - - - - - - - - - - - - - - - - - - P I T N S K - - - - - - - -   VC22
342  - - - - - - - - - - - - - - - - - - - - - - - - - - - L I T N S N S Q Y - - - - -   CRMB
238  - - - - - - - - - - - - - - - - - - - - - - - S H Y L S C T I V G I I V - - - - -   TNFR-like
```

```
                                                                              Consensus #1
449  - P L V E S L C S E S - - - - - - - - L P L G V P D A G M K P S - - - - - - -   TNFR1
448  P - - - - - - - - - - - - - - - - - - - - - - - - - - - - - - P A P S L L R    TNFR2
413  - - - - - - - - - - - - - - L A E T - E T L G C Q D L - - - - - - T A T S P V   NGFR
403  H - - - - - - - - - - - - - - - - - - - - - - - - - - - - - - - - - - - - -    LTbR
329  - I Q E D - Y R K P - - - - - - - - - - - - - - - - - - - - - N E I Q S L V     FAS
247  - Y P E Q E T E P P L G S C S - - - - - - - - - - - - - - - - E P A C S P       CD27
560  R - - - - - - - - - - - - - S D V M L S V E E E G K E D P L P T A A S G K       CD30
270  - Q E E D G C - - - - - - - - I S V Q - E R Q - - - - - - - - - - - - - - -     CD40
236  - I Q E E Q A D A H - - - - - R F P E E E E G - - - - - - - - - G C E L          4-1BB
263  - - - - - - - - - - - - - - - - - - - - - - - - - - - - - - - S T L A K I       OX40
349  - - - - - - - - - - - - - - - - - - - - - - - - - - - - - - - L - - - - - -     VC22
355  - - - - - - - - - - - - - - - - - - - - - - - - - - - - - - - L - - - - - -     CRMB
258  - - - - - - - - - - - - - - - - - - - - - - - - - - - - - - - - - F V - - -     TNFR-like
```

FIG.2P

HPRCB54R

```
  1 GAATTCGGCA NAGCCTCTCC ACGCGCACGA ACTCAGCCAA CGATTTCTGA
 51 TAGATTTTTG GGAGTTTGAC CAGAGATGCA AGGGGTGAAG GAGCGCTTCC
101 TACCGTTAGG AACTCTGGGG ACAGNNCGCC CCGGCCGCCT GATGGCCGAG
151 GCAGGGTGCG ACCCAGGACC CAGGACGGCG TCGGGAACCA TACCATGGCC
201 CGGATCCCCA AGACCCTAAA GTTCGTGGTC GTCATCGTCG CGGTCCTGCT
251 GCCAGTCCTA GCTTACTCTG CCACCACTGC CCGGCAGAGG AAGTTNCCCA
301 GCAGNCANTG GNCCCACAGC AACAGNGGCA CAGTTTCAAG GGGGNAGGAG
351 TTTTCCANCA AGTTTTTATA GTTCAGAACN TATTGGNGCT NTNAACCCTT
401 GCACAAGGGT TTGGNTTAAA CCAANGTTTC CAANATGNAC TTTTTNGTTC
451 CCTGTTANAT TTTTTAATTA GTTNAAANTT AAATTTNTNA ACCTTNCCNG
501 GGNAAATT
```

HSJAU57RA

```
  1 GGCAGAGGTG TCTCCAGCCT GGCTCTATCT TCCTCCTTGT NATCGTCCCA
 51 TCCCCACATC CCGTGCACCC CCCAGGACCC TGGTCTCATC AGTCCCTCTC
101 CTGGAGCTGG GGGTCCACAC ATCTCCCAGC CAAGTCCAAG AGGGCAGGGC
151 CAGTTCCTCC CATCTTCAGG CCCAGCCAGG CAGGGGGCAG TCGGCTCCTC
201 AACTGGGTGA CAAGGGTGAG GATGAGAAGT GGTCACGGGG ATTTATTCAG
251 CCTTGGTCAG AGCAGAACAC AGAGTTTTTC CGTGTGTTGG TTTTTACTCT
301 NNTTCCCCTT CTTNATNCCC CTTTCN
```

HUSCB54R

```
  1 CCAGGGTCTC CTNCCCCACC TGCTGAAGAG ACANTGACCA CCAGCCCGGG
 51 GACTCCTGCC TCTTCCTCAT TACCTCTNAT GNANCATCGT AGGGATCATA
101 GTTCTAATTG TGCCTTCTGA ATTGTGCTTT GTTTGGAAAG ACTTCACTGT
151 GGGAAGAAAT TCCTTCCTTA CCTGAAGTTG CAGGTAGGCC CTGGGTNAGG
201 GCGNGGGGCG CTGGACANTN TCTGGNCCTG GCTGCCCGCT G
```

HELBP70R

```
  1 GGCAGAGGCC CCAGCTGCTG AAGAGACAAT AATCACCAGC CCGGGGACTC
 51 CTGNNTCTNC TNATTACCTC TNATGCACCA TCGTAGGGAT CATAGTTCTA
101 ATTGTGCCTT CTAATTGTTT TTGTTTGAAA AGANTTCACT GTGGAAGAAA
151 TTCCTTCCTT ACCTGTAAGT TNCAGGTAGG NGCCTGGCTG AGGGCGGGGG
201 GCGCTGGTAC ACTCTCTGAC CCTGCCTCCC TCTGNCTGTT TTCCCACAGA
251 CAGAAACGCC TGCCCCTGNC CCCAAGTTCC TNGTGTTTTC CAGCCTGGCT
301 CTATCTTNNC TCCTTGTGAA TCGTTCCCAT CCCCACANGC
```

FIG.4

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 1392 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 183..959

(ix) FEATURE:
      (A) NAME/KEY: sig_peptide
      (B) LOCATION: 183..260

(ix) FEATURE:
    (A) NAME/KEY: mat_peptide
    (B) LOCATION: 261..959

(xi) SEQUENCE DESCRIPTION: SEQ ID NO: 1:

```
CCTCTCCACG CGCACGAACT CAGCCAACGA TTTCTGATAG ATTTTTGGGA GTTTGACCAG      60

AGATGCAAGG GGTGAAGGAG CGCTTCCTAC CGTTAGGGAA CTCTGGGGAC AGAGCGCCCC     120

GGCCGCCTGA TGGCCGAGGC AGGGTGCGAC CCAGGACCCA GGACGGCGTC GGGAACCATA     180

CC ATG GCC CGG ATC CCC AAG ACC CTA AAG TTC GTC GTC GTC ATC GTC        227
   Met Ala Arg Ile Pro Lys Thr Leu Lys Phe Val Val Val Ile Val
   -26 -25                 -20                 -15

GCG GTC CTG CTG CCA GTC CTA GCT TAC TCT GCC ACC ACT GCC CGG CAG       275
Ala Val Leu Leu Pro Val Leu Ala Tyr Ser Ala Thr Thr Ala Arg Gln
     -10                  -5                  1                   5

GAG GAA GTT CCC CAG CAG ACA GTG GCC CCA CAG CAA CAG AGG CAC AGC       323
Glu Glu Val Pro Gln Gln Thr Val Ala Pro Gln Gln Gln Arg His Ser
                 10                  15                  20

TTC AAG GGG GAG GAG TGT CCA GCA GGA TCT CAT AGA TCA GAA CAT ACT       371
Phe Lys Gly Glu Glu Cys Pro Ala Gly Ser His Arg Ser Glu His Thr
             25                  30                  35

GGA GCC TGT AAC CCG TGC ACA GAG GGT GTG GAT TAC ACC AAC GCT TCC       419
Gly Ala Cys Asn Pro Cys Thr Glu Gly Val Asp Tyr Thr Asn Ala Ser
         40                  45                  50

AAC AAT GAA CCT TCT TGC TTC CCA TGT ACA GTT TGT AAA TCA GAT CAA       467
Asn Asn Glu Pro Ser Cys Phe Pro Cys Thr Val Cys Lys Ser Asp Gln
     55                  60                  65

AAA CAT AAA AGT TCC TGC ACC ATG ACC AGA GAC ACA GTG TGT CAG TGT       515
Lys His Lys Ser Ser Cys Thr Met Thr Arg Asp Thr Val Cys Gln Cys
 70                  75                  80                  85

AAA GAA GGC ACC TTC CGG AAT GAA AAC TCC CCA GAG ATG TGC CGG AAG       563
Lys Glu Gly Thr Phe Arg Asn Glu Asn Ser Pro Glu Met Cys Arg Lys
                 90                  95                 100

TGT AGC AGG TGC CCT AGT GGG GAA GTC CAA GTC AGT AAT TGT ACG TCC       611
Cys Ser Arg Cys Pro Ser Gly Glu Val Gln Val Ser Asn Cys Thr Ser
             105                 110                 115

TGG GAT GAT ATC CAG TGT GTT GAA GAA TTT GGT GCC AAT GCC ACT GTG       659
Trp Asp Asp Ile Gln Cys Val Glu Glu Phe Gly Ala Asn Ala Thr Val
         120                 125                 130

GAA ACC CCA GCT GCT GAA GAG ACA ATG AAC ACC AGC CCG GGG ACT CCT       707
Glu Thr Pro Ala Ala Glu Glu Thr Met Asn Thr Ser Pro Gly Thr Pro
     135                 140                 145

GCC CCA GCT GCT GAA GAG ACA ATG AAC ACC AGC CCA GGG ACT CCT GCC       755
Ala Pro Ala Ala Glu Glu Thr Met Asn Thr Ser Pro Gly Thr Pro Ala
150                 155                 160                 165

CCA GCT GCT GAA GAG ACA ATG ACC ACC AGC CCG GGG ACT CCT GCC CCA       803
Pro Ala Ala Glu Glu Thr Met Thr Thr Ser Pro Gly Thr Pro Ala Pro
                 170                 175                 180

GCT GCT GAA GAG ACA ATG ACC ACC AGC CCG GGG ACT CCT GCC CCA GCT       851
Ala Ala Glu Glu Thr Met Thr Thr Ser Pro Gly Thr Pro Ala Pro Ala
             185                 190                 195

GCT GAA GAG ACA ATG ACC ACC AGC CCG GGG ACT CCT GCC TCT TCT CAT       899
Ala Glu Glu Thr Met Thr Thr Ser Pro Gly Thr Pro Ala Ser Ser His
         200                 205                 210

TAC CTC TCA TGC ACC ATC GTA GGG ATC ATA GTT CTA ATT GTG CTT CTG       947
Tyr Leu Ser Cys Thr Ile Val Gly Ile Ile Val Leu Ile Val Leu Leu
     215                 220                 225
```

-continued

```
ATT GTG TTT GTT TGAAAGACTT CACTGTGGAA GAAATTCCTT CCTTACCTGA     999
Ile Val Phe Val
230

AAGGTTCAGG TAGGCGCTGG CTGAGGGCGG GGGGCGCTGG ACACTCTCTG CCCTGCCTCC  1059

CTCTGCTGTG TTCCCACAGA CAGAAACGCC TGCCCCTGCC CCAAGTCCTG GTGTCTCCAG  1119

CCTGGCTCTA TCTTCCTCCT TGTGATCGTC CCATCCCCAC ATCCCGTGCA CCCCCCAGGA  1179

CCCTGGTCTC ATCAGTCCCT CTCCTGGAGC TGGGGGTCCA CACATCTCCC AGCCAAGTCC  1239

AAGAGGCAGG GCCAGTTCCT CCCATCTTCA GGCCCAGCCA GGCAGGGGGC AGTCGGCTCC  1299

TCAACTGGGT GACAAGGGTG AGGATGAGAA GTGGTCACGG GATTTATTCA GCCTTGGTCA  1359

GAGCAGAACA CAGAGATTTT CCGTGAAAAA AAA                              1392
```

(2) INFORMATION FOR SEQ ID NO: 2:

(i) SEQUENCE CHARACTERISTICS:
        (A) LENGTH: 259 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Arg Ile Pro Lys Thr Leu Lys Phe Val Val Ile Val Ala
-26 -25             -20             -15

Val Leu Leu Pro Val Leu Ala Tyr Ser Ala Thr Thr Ala Arg Gln Glu
-10          -5                   1                   5

Glu Val Pro Gln Gln Thr Val Ala Pro Gln Gln Arg His Ser Phe
             10                  15                  20

Lys Gly Glu Glu Cys Pro Ala Gly Ser His Arg Ser Glu His Thr Gly
             25                  30                  35

Ala Cys Asn Pro Cys Thr Glu Gly Val Asp Tyr Thr Asn Ala Ser Asn
         40              45              50

Asn Glu Pro Ser Cys Phe Pro Cys Thr Val Cys Lys Ser Asp Gln Lys
55              60              65                  70

His Lys Ser Ser Cys Thr Met Thr Arg Asp Thr Val Cys Gln Cys Lys
                75              80              85

Glu Gly Thr Phe Arg Asn Glu Asn Ser Pro Glu Met Cys Arg Lys Cys
            90              95              100

Ser Arg Cys Pro Ser Gly Glu Val Gln Val Ser Asn Cys Thr Ser Trp
        105             110             115

Asp Asp Ile Gln Cys Val Glu Glu Phe Gly Ala Asn Ala Thr Val Glu
    120             125             130

Thr Pro Ala Ala Glu Glu Thr Met Asn Thr Ser Pro Gly Thr Pro Ala
135             140             145             150

Pro Ala Ala Glu Glu Thr Met Asn Thr Ser Pro Gly Thr Pro Ala Pro
            155             160             165

Ala Ala Glu Glu Thr Met Thr Thr Ser Pro Gly Thr Pro Ala Pro Ala
            170             175             180

Ala Glu Glu Thr Met Thr Thr Ser Pro Gly Thr Pro Ala Pro Ala Ala
        185             190             195

Glu Glu Thr Met Thr Thr Ser Pro Gly Thr Pro Ala Ser Ser His Tyr
        200             205             210

Leu Ser Cys Thr Ile Val Gly Ile Ile Val Leu Ile Val Leu Leu Ile
215             220             225             230

Val Phe Val
```

(2) INFORMATION FOR SEQ ID NO: 3:

(i) SEQUENCE CHARACTERISTICS:
        (A) LENGTH: 455 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Met Gly Leu Ser Thr Val Pro Asp Leu Leu Pro Leu Val Leu Leu
 1               5                  10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
         35                  40                  45

Tyr Ile His Pro Gln Asn Asn Ser Ile Cys Cys Thr Lys Cys His Lys
 50                  55                  60

Gly Thr Tyr Leu Tyr Asn Asp Cys Pro Gly Pro Gly Gln Asp Thr Asp
 65              70                  75                      80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
                100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Ser Thr Tyr Thr Pro Gly Asp Cys
            290                 295                 300

Pro Asn Phe Ala Ala Pro Arg Arg Glu Val Ala Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
                340                 345                 350
```

-continued

```
Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
                420                 425                 430

Cys Leu Glu Asp Ile Glu Glu Ala Leu Cys Gly Pro Ala Ala Leu Pro
            435                 440                 445

Pro Ala Pro Ser Leu Leu Arg
450                 455

(2) INFORMATION FOR SEQ ID NO: 4:

(i) SEQUENCE CHARACTERISTICS:
        (A) LENGTH: 461 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240
```

```
Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
        260                 265                 270

Leu Leu Ile Ile Gly Val Val Asn Cys Val Ile Met Thr Gln Val Lys
            275                 280                 285

Lys Lys Pro Leu Cys Leu Gln Arg Glu Ala Lys Val Pro His Leu Pro
        290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
                355                 360                 365

Asp Ser Ser Pro Gly Gly His Gly Thr Gln Val Asn Val Thr Cys Ile
        370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
                435                 440                 445

Leu Pro Leu Gly Val Pro Asp Ala Gly Met Lys Pro Ser
450                 455                 460

(2) INFORMATION FOR SEQ ID NO: 5:

(i) SEQUENCE CHARACTERISTICS:
        (A) LENGTH: 427 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
            85                  90                  95

Ala Pro Cys Val Glu Ala Asp Asp Ala Val Cys Arg Cys Ala Tyr Gly
        100                 105                 110

Tyr Tyr Gln Asp Glu Thr Thr Gly Arg Cys Glu Ala Cys Arg Val Cys
    115                 120                 125
```

```
Glu Ala Gly Ser Gly Leu Val Phe Ser Cys Gln Asp Lys Gln Asn Thr
    130                 135                 140
Val Cys Glu Glu Cys Pro Asp Gly Thr Tyr Ser Asp Glu Ala Asn His
145                 150                 155                 160
Val Asp Pro Cys Leu Pro Cys Thr Val Cys Glu Asp Thr Glu Arg Gln
                165                 170                 175
Leu Arg Glu Cys Thr Arg Trp Ala Asp Ala Glu Cys Glu Glu Ile Pro
            180                 185                 190
Gly Arg Trp Ile Thr Arg Ser Thr Pro Pro Glu Gly Ser Asp Ser Thr
        195                 200                 205
Ala Pro Ser Thr Gln Glu Pro Glu Ala Pro Pro Glu Gln Asp Leu Ile
    210                 215                 220
Ala Ser Thr Val Ala Gly Val Val Thr Thr Val Met Gly Ser Ser Gln
225                 230                 235                 240
Pro Val Val Thr Arg Gly Thr Thr Asp Asn Leu Ile Pro Val Tyr Cys
                245                 250                 255
Ser Ile Leu Ala Ala Val Val Val Gly Leu Val Ala Tyr Ile Ala Phe
            260                 265                 270
Lys Arg Trp Asn Ser Cys Lys Gln Asn Lys Gln Gly Ala Asn Ser Arg
        275                 280                 285
Pro Val Asn Gln Thr Pro Pro Pro Glu Gly Glu Lys Leu His Ser Asp
    290                 295                 300
Ser Gly Ile Ser Val Asp Ser Gln Ser Leu His Asp Gln Gln Pro His
305                 310                 315                 320
Thr Gln Thr Ala Ser Gly Gln Ala Leu Lys Gly Asp Gly Gly Leu Tyr
                325                 330                 335
Ser Ser Leu Pro Pro Ala Lys Arg Glu Glu Val Glu Lys Leu Leu Asn
            340                 345                 350
Gly Ser Ala Gly Asp Thr Trp Arg His Leu Ala Gly Glu Leu Gly Tyr
        355                 360                 365
Gln Pro Glu His Ile Asp Ser Phe Thr His Glu Ala Cys Pro Val Arg
    370                 375                 380
Ala Leu Leu Ala Ser Trp Ala Thr Gln Asp Ser Ala Thr Leu Asp Ala
385                 390                 395                 400
Leu Leu Ala Ala Leu Arg Arg Ile Gln Arg Ala Asp Leu Val Glu Ser
                405                 410                 415
Leu Cys Ser Glu Ser Thr Ala Thr Ser Pro Val
            420                 425

(2) INFORMATION FOR SEQ ID NO: 6:

(i) SEQUENCE CHARACTERISTICS:
        (A) LENGTH: 415 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Met Arg Leu Pro Arg Ala Ser Ser Pro Cys Gly Leu Ala Trp Gly Pro
1               5                   10                  15
Leu Leu Leu Gly Leu Ser Gly Leu Leu Val Ala Ser Gln Pro Gln Leu
                20                  25                  30
Val Pro Pro Tyr Arg Ile Glu Asn Gln Thr Cys Trp Asp Gln Asp Lys
            35                  40                  45
```

```
Glu Tyr Tyr Glu Pro Met His Asp Val Cys Cys Ser Arg Cys Pro Pro
 50                  55                  60
Gly Glu Phe Val Phe Ala Val Cys Ser Arg Ser Gln Asp Thr Val Cys
 65                  70                  75                  80
Lys Thr Cys Pro His Asn Ser Tyr Asn Glu His Trp Asn His Leu Ser
                     85                  90                  95
Thr Cys Gln Leu Cys Arg Pro Cys Asp Ile Val Leu Gly Phe Glu Glu
                100                 105                 110
Val Ala Pro Cys Thr Ser Asp Arg Lys Ala Glu Cys Arg Cys Gln Pro
                115                 120                 125
Gly Met Ser Cys Val Tyr Leu Asp Asn Glu Cys Val His Cys Glu Glu
                130                 135                 140
Glu Arg Leu Val Leu Cys Gln Pro Gly Thr Glu Ala Glu Val Thr Asp
145                 150                 155                 160
Glu Ile Met Asp Thr Asp Val Asn Cys Val Pro Cys Lys Pro Gly His
                165                 170                 175
Phe Gln Asn Thr Ser Ser Pro Arg Ala Arg Cys Gln Pro His Thr Arg
                180                 185                 190
Cys Glu Ile Gln Gly Leu Val Glu Ala Ala Pro Gly Thr Ser Tyr Ser
                195                 200                 205
Asp Thr Ile Cys Lys Asn Pro Pro Glu Pro Gly Ala Met Leu Leu Leu
                210                 215                 220
Ala Ile Leu Leu Ser Leu Val Leu Phe Leu Leu Phe Thr Thr Val Leu
225                 230                 235                 240
Ala Cys Ala Trp Met Arg His Pro Ser Leu Cys Arg Lys Leu Gly Thr
                245                 250                 255
Leu Leu Lys Arg His Pro Glu Gly Glu Glu Ser Pro Pro Cys Pro Ala
                260                 265                 270
Pro Arg Ala Asp Pro His Phe Pro Asp Leu Ala Glu Pro Leu Leu Pro
                275                 280                 285
Met Ser Gly Asp Leu Ser Pro Ser Pro Ala Gly Pro Pro Thr Ala Pro
                290                 295                 300
Ser Leu Glu Glu Val Val Leu Gln Gln Gln Ser Pro Leu Val Gln Ala
305                 310                 315                 320
Arg Glu Leu Glu Ala Glu Pro Gly Glu His Gly Gln Val Ala His Gly
                325                 330                 335
Ala Asn Gly Ile His Val Thr Gly Gly Ser Val Thr Val Thr Gly Asn
                340                 345                 350
Ile Tyr Ile Tyr Asn Gly Pro Val Leu Gly Gly Thr Arg Gly Pro Gly
                355                 360                 365
Asp Pro Pro Ala Pro Pro Glu Pro Pro Tyr Pro Thr Pro Glu Glu Gly
                370                 375                 380
Ala Pro Gly Pro Ser Glu Leu Ser Thr Pro Tyr Gln Glu Asp Gly Lys
385                 390                 395                 400
Ala Trp His Leu Ala Glu Thr Glu Thr Leu Gly Cys Gln Asp Leu
                405                 410                 415

(2) INFORMATION FOR SEQ ID NO: 7:

(i) SEQUENCE CHARACTERISTICS:
        (A) LENGTH: 335 amino acids
        (B) TYPE: amino acid
        (C) STRANDEDNESS: single
        (D) TOPOLOGY: linear
```

(ii) MOLECULE TYPE: protein (xi) SEQUENCE DESCRIPTION: SEQ ID NO: 7:

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65              70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
                100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
            195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
                260                 265                 270

Gln Lys Val Gln Leu Leu Arg Asn Trp His Gln Leu His Gly Lys Lys
            275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

(2) INFORMATION FOR SEQ ID NO: 8:

(i) SEQUENCE CHARACTERISTICS:
        (A) LENGTH: 260 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

-continued

```
Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
            195                 200                 205

Leu Phe Leu His Gln Arg Arg Lys Tyr Arg Ser Asn Lys Gly Glu Ser
        210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260
```

(2) INFORMATION FOR SEQ ID NO: 9:

(i) SEQUENCE CHARACTERISTICS:
        (A) LENGTH: 595 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
        50                  55                  60

Cys Arg Lys Gln Cys Glu Pro Asp Tyr Tyr Leu Asp Glu Ala Asp Arg
65                  70                  75                  80
```

-continued

```
Cys Thr Ala Cys Val Thr Cys Ser Arg Asp Asp Leu Val Glu Lys Thr
                 85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495
```

```
Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
            515                 520                 525

Thr Val Lys Ala Glu Leu Pro Glu Gly Arg Gly Leu Ala Gly Pro Ala
            530                 535                 540

Glu Pro Glu Leu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590

Ser Gly Lys
        595

(2) INFORMATION FOR SEQ ID NO: 10:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65              70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
        130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
        210                 215                 220

Lys Ala Pro His Pro Lys Gln Glu Pro Gln Glu Ile Asn Phe Pro Asp
225                 230                 235                 240
```

```
Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

(2) INFORMATION FOR SEQ ID NO: 11:

(i) SEQUENCE CHARACTERISTICS:
        (A) LENGTH: 255 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Arg Asn Gln Ile Cys Ser Pro Cys
            35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

(2) INFORMATION FOR SEQ ID NO: 12:

(i) SEQUENCE CHARACTERISTICS:
        (A) LENGTH: 277 amino acids
        (B) TYPE: amino acid
        (C) STRANDEDNESS: single
        (D) TOPOLOGY: linear
```

```
    (ii) MOLECULE TYPE: protein (xi) SEQUENCE DESCRIPTION: SEQ ID NO: 12:

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275

(2) INFORMATION FOR SEQ ID NO: 13:

(i) SEQUENCE CHARACTERISTICS:
        (A) LENGTH: 349 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

Met Lys Ser Val Leu Tyr Leu Tyr Ile Leu Phe Leu Ser Cys Ile Ile
1               5                   10                  15

Ile Asn Gly Arg Asp Ala Ala Pro Tyr Thr Pro Asn Gly Lys Cys
            20                  25                  30

Lys Asp Thr Glu Tyr Lys Arg His Asn Leu Cys Cys Leu Ser Cys Pro
            35                  40                  45
```

```
Pro Gly Thr Tyr Ala Ser Arg Leu Cys Asp Ser Lys Thr Asn Thr Gln
    50                  55                  60

Cys Thr Pro Cys Gly Ser Gly Thr Phe Thr Ser Arg Asn Asn His Leu
 65                  70                  75                  80

Pro Ala Cys Leu Ser Cys Asn Gly Arg Cys Asn Ser Asn Gln Val Glu
                 85                  90                  95

Thr Arg Ser Cys Asn Thr Thr His Asn Arg Ile Cys Glu Cys Ser Pro
                100                 105                 110

Gly Tyr Tyr Cys Leu Leu Lys Gly Ser Ser Gly Cys Lys Ala Cys Val
            115                 120                 125

Ser Gln Thr Lys Cys Gly Ile Gly Tyr Gly Val Ser Gly His Thr Ser
    130                 135                 140

Val Gly Asp Val Ile Cys Ser Pro Cys Gly Phe Gly Thr Tyr Ser His
145                 150                 155                 160

Thr Val Ser Ser Ala Asp Lys Cys Glu Pro Val Pro Asn Asn Thr Phe
                165                 170                 175

Asn Tyr Ile Asp Val Glu Ile Thr Leu Tyr Pro Val Asn Asp Thr Ser
            180                 185                 190

Cys Thr Arg Thr Thr Thr Thr Gly Leu Ser Glu Ser Ile Leu Thr Ser
            195                 200                 205

Glu Leu Thr Ile Thr Met Asn His Thr Asp Cys Asn Pro Val Phe Arg
    210                 215                 220

Glu Glu Tyr Phe Ser Val Leu Asn Lys Val Ala Thr Ser Gly Phe Phe
225                 230                 235                 240

Thr Gly Glu Asn Arg Tyr Gln Asn Ile Ser Lys Val Cys Thr Leu Asn
                245                 250                 255

Phe Glu Ile Lys Cys Asn Asn Lys Gly Ser Ser Phe Lys Gln Leu Thr
                260                 265                 270

Lys Ala Lys Asn Asp Asp Gly Met Met Ser His Ser Glu Thr Val Thr
            275                 280                 285

Leu Ala Gly Asp Cys Leu Ser Ser Val Asp Ile Tyr Ile Leu Tyr Ser
    290                 295                 300

Asn Thr Asn Ala Gln Asp Tyr Glu Thr Asp Thr Ile Ser Tyr Arg Val
305                 310                 315                 320

Gly Asn Val Leu Asp Asp Asp Ser His Met Pro Gly Ser Cys Asn Ile
                325                 330                 335

His Lys Pro Ile Thr Asn Ser Lys Pro Thr Arg Phe Leu
            340                 345

(2) INFORMATION FOR SEQ ID NO: 14:

(i) SEQUENCE CHARACTERISTICS:
        (A) LENGTH: 355 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

Met Lys Ser Tyr Ile Leu Leu Leu Leu Ser Cys Ile Ile Ile
 1               5                  10                  15

Asn Ser Asp Ile Thr Pro His Glu Pro Ser Asn Gly Lys Cys Lys Asp
                 20                  25                  30

Asn Glu Tyr Lys Arg His His Leu Cys Cys Leu Ser Cys Pro Pro Gly
             35                  40                  45
```

```
Thr Tyr Ala Ser Arg Leu Cys Asp Ser Lys Thr Asn Thr Asn Thr Gln
     50                  55                  60

Cys Thr Pro Cys Ala Ser Asp Thr Phe Thr Ser Arg Asn Asn His Leu
 65              70                  75                      80

Pro Ala Cys Leu Ser Cys Asn Gly Arg Cys Asp Ser Asn Gln Val Glu
                 85                  90                  95

Thr Arg Ser Cys Asn Thr Thr His Asn Arg Ile Cys Asp Cys Ala Pro
                100             105             110

Gly Tyr Tyr Cys Phe Leu Lys Gly Ser Gly Cys Lys Ala Cys Val
            115             120             125

Ser Gln Thr Lys Cys Gly Ile Gly Tyr Gly Val Ser Gly His Thr Pro
    130             135             140

Thr Gly Asp Val Val Cys Ser Pro Cys Gly Leu Gly Thr Tyr Ser His
145             150             155                         160

Thr Val Ser Ser Val Asp Lys Cys Glu Pro Val Pro Ser Asn Thr Phe
                165             170             175

Asn Tyr Ile Asp Val Glu Ile Asn Leu Tyr Pro Val Asn Asp Thr Ser
            180             185             190

Cys Thr Arg Thr Thr Thr Gly Leu Ser Glu Ser Ile Ser Thr Ser
            195             200             205

Glu Leu Thr Ile Thr Met Asn His Lys Asp Cys Asp Pro Val Phe Arg
    210             215             220

Asn Gly Tyr Phe Ser Val Leu Asn Glu Val Ala Thr Ser Gly Phe Phe
225             230             235             240

Thr Gly Gln Asn Arg Tyr Gln Asn Ile Ser Lys Val Cys Thr Leu Asn
            245             250             255

Phe Glu Ile Lys Cys Asn Asn Lys Asp Ser Tyr Ser Ser Lys Gln
            260             265             270

Leu Thr Lys Thr Lys Asn Asp Asp Ser Ile Met Pro His Ser Glu
    275             280             285

Ser Val Thr Leu Val Gly Asp Cys Leu Ser Ser Val Asp Ile Tyr Ile
    290             295             300

Leu Tyr Ser Asn Thr Asn Thr Gln Asp Tyr Glu Thr Asp Thr Ile Ser
305             310             315             320

Tyr His Val Gly Asn Val Leu Asp Val Asp Ser His Met Pro Gly Arg
                325             330             335

Cys Asp Thr His Lys Leu Ile Thr Asn Ser Asn Ser Gln Tyr Pro Thr
            340             345             350

His Phe Leu
        355

(2) INFORMATION FOR SEQ ID NO: 15:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GAATTCGGCA NAGCCTCTCC ACGCGCAGAA CTCAGCCAAC GATTTCTGAT AGATTTTTGG      60

GAGTTTGACC AGAGATGCAA GGGGTGAAGG AGCGCTTCCT ACCGTTAGGA ACTCTGGGGA     120

CAGNNCGCCC CGGCCGCCTG ATGGCCGAGG CAGGGTGCGA CCCAGGACCC AGGACGGCGT     180
```

```
CGGGAACCAT ACCATGGCCC GGATCCCCAA GACCCTAAAG TTCGTGGTCG TCATCGTCGC      240

GGTCCTGCTG CCAGTCCTAG CTTACTCTGC CACCACTGCC CGGCAGAGGA AGTTNCCCAG      300

CAGNCANTGG NCCCACAGCA ACAGNGGCAC AGTTTCAAGG GGGNAGGAGT TTTCCANCAA      360

GTTTTTATAG TTCAGAACNT ATTGGNGCTN TNAACCCTTG CACAAGGGTT TGGNTTAAAC      420

CAANGTTTCC AANATGNACT TTTTNGTTCC CTGTTANATT TTTTAATTAG TTNAANTTAA      480

ATTTNTNAAC CTTNCCNGGG NAAATT                                          506

(2) INFORMATION FOR SEQ ID NO: 16:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

GGCAGAGGTG TCTCCAGCCT GGCTCTATCT TCCTCCTTGT NATCGTCCCA TCCCCACATC       60

CCGTGCACCC CCCAGGACCC TGGTCTCATC AGTCCCTCTC CTGGAGCTGG GGGTCCACAC      120

ATCTCCCAGC CAAGTCCAAG AGGGCAGGGC CAGTTCCTCC CATCTTCAGG CCCAGCCAGG      180

CAGGGGGCAG TCGGCTCCTC AACTGGGTGA CAAGGGTGAG GATGAGAAGT GGTCACGGGG      240

ATTTATTCAG CCTTGGTCAG AGCAGAACAC AGATTTTTCC GTGTGTTGGT TTTTACTCTN      300

NTTCCCCTTC TTNATNCCCC TTTCN                                           325

(2) INFORMATION FOR SEQ ID NO: 17:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GGCAGAGGCC CCAGCTGCTG AAGAGACAAT AATCACCAGC CCGGGGACTC CTGNNTCTNC       60

TNATTACCTC TNATGCACCA TCGTAGGGAT CATAGTTCTA ATTGTGCCTT CTAATTGTTT      120

TTGTTTGAAA AGANTTCACT GTGGAAGAAA TTCCTTCCTT ACCTGTAAGT TNCAGGTAGG      180

NGCCTGGCTG AGGGCGGGGG GCGCTGGTAC ACTCTCTGAC CCTGCCTCCC TCTGNCTGTT      240

TTCCCACAGA CAGAAACGCC TGCCCCTGNC CCCAAGTTCC TNGTGTTTTC CAGCCTGGCT      300

CTATCTTNNC TCCTTGTGAA TCGTTCCCAT CCCCACANGC                            340

(2) INFORMATION FOR SEQ ID NO: 18:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

CCAGGGTCTC CTNCCCCACC TGCTGAAGAG ACANTGACCA CCAGCCCGGG GACTCCTGCC       60

TCTTCCTCAT TACCTCTNAT GNANCATCGT AGGGATCATA GTTCTAATTG TGCCTTCTGA      120
```

```
ATTGTGCTTT GTTTGGAAAG ACTTCACTGT GGGAAGAAAT TCCTTCCTTA CCTGAAGTTG        180

CAGGTAGGCC CTGGGTNAGG GCGNGGGGCG CTGGACANTN TCTGGNCCTG GCTGCCCGCT        240

G                                                                      241
```

(2) INFORMATION FOR SEQ ID NO: 19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
CGCGGATCCA CCACTGCCCG GCAGGAG                                           27
```

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
GCGTCTAGAC TAGTAATGAG AAGAGGCAGG                                        30
```

(2) INFORMATION FOR SEQ ID NO: 21:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
CGCTCTAGAC CGCCATCATG GCCCGGATCC CCAAG                                  35
```

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

```
GCGTCTAGAC TAGTAATGAG AAGAGGCAGG                                        30
```

(2) INFORMATION FOR SEQ ID NO: 23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO: 23:

CGCGAATTCC GCCATCATGG CCCGGATCCC CAAG                                      34

(2) INFORMATION FOR SEQ ID NO: 24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

GCGTCTAGAG TAATGAGAAG AGGCAGG                                              27

(2) INFORMATION FOR SEQ ID NO: 25:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

CGCTCTAGAC CGCCATCATG GCCCGGATCC CCAAG                                     35

(2) INFORMATION FOR SEQ ID NO: 26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

GCGTCTAGAC TAGTAATGAG AAGAGGCAGG                                           30

NUCLEIC ACIDS ENCODING TUMOR NECROSIS FACTOR RECEPTOR 5

This application claims benefit of 35 U.S.C. section 119(e) based on U.S. Provisional Application Ser. No. 60/035,496, filed Jan. 14, 1997 and No. 60/054,885, filed Aug. 7, 1997.

FIELD OF THE INVENTION

The present invention relates to a novel human gene encoding a polypeptide which is a member of the TNF receptor family, and has now been found to bind TRAIL. More specifically, an isolated nucleic acid molecule is provided encoding a human polypeptide named tumor necrosis factor receptor-5, sometimes referred to as "TNFR-5" or "TR5," and now referred to as hereinafter as "TRAIL receptor without intracellular domain" or "TRID." TRID polypeptides are also provided, as are vectors, host cells, and recombinant methods for producing the same. The invention further relates to screening methods for identifying agonists or antagonists of TRID polypeptide activity. Also provided are diagnostic and therapeutic methods utilizing such compositions.

RELATED ART

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines, which act through TNF receptors to regulate numerous biological processes, including protection against infection and induction of shock and inflammatory disease. The TNF molecules belong to the "TNF-ligand" superfamily, and act together with theirreceptors or counter-ligands, the "TNF-receptor" superfamily. So far, nine members of the TNF ligand superfamily have been identified and ten members of the TNF-receptor superfamily have been characterized.

Among the ligands, there are included TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (Meager, A., *Biologicals* 22:291–295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R. et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen, R. C. et al., *Science* 259:990 (1993)). Targeted mutations of the low affinity nerve growth factor receptor cause a disorder characterized by faulty sensory innovation of peripheral structures (Lee, K. F. et al., *Cell* 69:737 (1992)).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (Beutler, B. and Von Huffel, C., *Science* 264:667–668 (1994)). Mutations in the p55 Receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., *Cell* 74:845 (1993)).

Apoptosis, or programmed cell death, is a physiologic process essential for the normal development and homeostasis of multicellular organisms (H. Steller, *Science* 267, 1445–1449 (1995)). Derangements of apoptosis contribute to the pathogenesis of several human diseases including cancer, neurodegenerative disorders, and acquired immune deficiency syndrome (C. B. Thompson, *Science* 267, 1456–1462 (1995)). One mechanism of immune mediated killing is the engagement of death receptors. Recently, much attention has focused on the signal transduction and biological function of two cell surface death receptors, Fas/APO-1 and TNFR-1 (J. L. Cleveland et al., *Cell* 81, 479–482 (1995); A. Fraser, et al., *Cell* 85, 781–784 (1996); S. Nagata et al., *Science* 267, 1449–56 (1995)). Both are members of the TNF receptor family which also include TNFR-2, low affinity NGFR, CD40, and CD30, among others (C. A. Smith et al., *Science* 248, 1019–23 (1990); M. Tewari et al., in *Modular Texts in Molecular and Cell Biology* M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain", which is distantly related to the Drosophila suicide gene, reaper (P. Golstein, et al., *Cell* 81, 185–186 (1995); K. White et al., *Science* 264, 677–83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan et al., *Cell* 81, 505–12(1995); M. P. Boldin et al., *J Biol Chem* 270, 7795–8 (1995); F. C. Kischkel et al., *EMBO* 14, 5579–5588 (1995)), which in turn binds and presumably activates FLICE/MACH1, a member of the ICE/CED-3 family of pro-apoptotic proteases (M. Muzio et al., *Cell* 85, 817–827 (1996); M. P. Boldin et al., *Cell* 85, 803–815 (1996)). While the central role of Fas/APO-1 is to trigger cell death, TNFR-1 can signal an array of diverse biological activities-many of which stem from its ability to activate NF-kB (L. A. Tartagliaetal., *Immunol Today* 13, 151–3 (1992)). Accordingly, TNFR-1 recruits the multivalent adapter molecule TRADD, which like FADD, also contains a death domain (H. Hsu et al., *Cell* 81, 495–504 (1995); H. Hsu, et al., *Cell* 84, 299–308 (1996)). Through its associations with a number of signaling molecules including FADD, TRAF2, and RIP, TRADD can signal both apoptosis and NF-kB activation (H. Hsu et al., *Cell* 84, 299–308 (1996); H. Hsu, et al., *Immunity* 4, 387–396 (1996)).

Recently, a new apoptosis-inducing TNF ligand has been discovered. S. R. Wiley et al., *Immunity* 3,673–682 (1995) named the molecule—"TNF-related apoptosis-inducing ligand" or simply "TRAIL." The molecule has also been called "Apo-2 ligand" or "Apo-2L." R. M. Pitt et al., *J Biol. Chem.* 271,12687–12690 (1996). This molecule was also disclosed in co-pending U.S. provisional application No. 60/013,405. For convenience, the molecule will be referred to herein as TRAIL.

Unlike FAS ligand, whose transcripts appear to be largely restricted to stimulated T-cells, significant levels of TRAIL are detected in many human tissues (e.g., spleen, lung, prostate, thymus, ovary, small intestine, colon, peripheral blood lymphocytes, placenta, kidney), and is constitutively transcribed by some cell lines. It has been shown that TRAIL acts independently from the Fas ligand (Wiley et al., supra). It has also been shown that TRAIL activates apoptosis rapidly, within a time frame that is similar to death signalling by Fas/Apo-1L, but much faster than TNF-induced apoptosis. S. A. Marsters et al., *Current Biology* 6, 750–752 (1996). The inability of TRAIL to bind TNFR-1, Fas, or the recently identified DR3, suggests that TRAIL may interact with a unique receptor(s).

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize additional novel receptors that bind TRAIL.

SUMMARY OF THE INVENTION

The present invention provides isolated nucleic acid molecules comprising a polynucleotide encoding the TRID polypeptide having the amino acid sequence shown in SEQ ID NO:2, or the amino acid sequence encoded by the cDNA clone deposited as ATCC Deposit Number 97798 on Nov. 20, 1996. The nucleotide sequence determined by sequencing the deposited TRID clone, which is shown in SEQ ID NO:1 contains an open reading frame encoding a polypeptide of about 259 amino acid residues, with a leader sequence of about 26 amino acids.

The present invention also relates to recombinant vectors, which include the isolated nucleic acid molecules of the present invention, and to host cells containing the recombinant vectors, as well as to methods of making such vectors and host cells and methods for using them for production of TRID polypeptides or peptides by recombinant techniques.

The invention further provides an isolated TRID polypeptide having an amino acid sequence encoded by a polynucleotide described herein.

The present invention also provides diagnostic assays such as quantitative and diagnostic assays for detecting levels of TRID protein. Thus, for instance, a diagnostic assay in accordance with the invention for detecting expression of TRID, or soluble form thereof, may be used to detect the ability of normal tissue to withstand or be protected from the deleterious effects of TRAIL, such as TRAIL-induced apoptosis.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. Cellular response to TNF-family ligands include not only normal physiological responses, but also diseases associated with increased apoptosis or the inhibition of apoptosis. Apoptosis—programmed cell death—is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft vs. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia and anorexia.

Thus, the invention further provides a method for enhancing apoptosis induced by a TNF-family ligand, such as TRAIL, which involves administering to a cell which expresses the TRID polypeptide an effective amount of an antagonist capable of decreasing TRID's ability to bind TRAIL. Preferably, TRID binding is decreased to treat a disease wherein decreased apoptosis is exhibited.

In a further aspect, the present invention is directed to a method for enhancing apoptosis induced by a TNF-family ligand, such as TRAIL, which involves administering to a cell an effective amount of TRID or an agonist capable of increasing TRID activity. Preferably, TRID activity is increased to treat a disease wherein decreased apoptosis is exhibited.

Whether any candidate "agonist" or "antagonist" of the present invention can enhance or inhibit apoptosis can be determined using art-known TNF-family ligand/receptor cellular response assays, including those described in more detail below. Thus, in a further aspect, a screening method is provided for determining whether a candidate agonist or antagonist is capable of enhancing or inhibiting a cellular response to a TNF-family ligand, such as TRAIL. The method involves contacting cells which co-expresses the TRID polypeptide and a second TNFR with a candidate compound and a TNF-family ligand (e.g., TRAIL), assaying a cellular response, and comparing the cellular response to a standard cellular response, the standard being assayed when contact is made with the ligand in absence of the candidate compound, whereby an increased cellular response over the standard indicates that the candidate compound is a TRID antagonist and a decreased cellular response compared to the standard indicates that the candidate compound is TRID agonist. By the invention, a cell expressing the TNFR polypeptide can be contacted with either an endogenous or exogenously administered TNF-family ligand, such as TRAIL.

BRIEF DESCRIPTION OF THE FIGURES

FIGS. 1A and 1B show the nucleotide sequence (SEQ ID NO:1) and deduced amino acid sequence (SEQ ID NO:2) of TRID.

FIGS. 2A–2P show an alignment created by the Clustal method using the Megaline program in the DNAstar suite comparing the amino acid sequences of TNFR-5 (now called "TRID," denoted as "TNFR-like" in the figure), with other TNF receptors, as follows: TNFR1 (SEQ ID NO:3); TNFR2 (SEQ ID NO:4); NGFR (SEQ ID NO:5) LTbR (SEQ ID NO:6); FAS (SEQ ID NO:7); CD27 (SEQ ID NO:8); CD30 (SEQ ID NO:9); CD40 (SEQ ID NO:10); 4-1BB (SEQ ID NO:11); OX40 (SEQ ID NO:12); VC22 (SEQ ID NO:13); and CRMB (SEQ ID NO:14).

FIG. 4 shows the nucleotide sequence of gene fragments related to the TRID gene of the present invention, including: HPRCB54R (SEQ ID NO:15), HSJAU57RA (SEQ ID NO:16), HELBP70R (SEQ ID NO:17), and HUSCB54R (SEQ ID NO:18) all of which are related to SEQ ID NO:1.

DETAILED DESCRIPTION OF THE PREFERRED EMBODIMENTS

Figure 3:
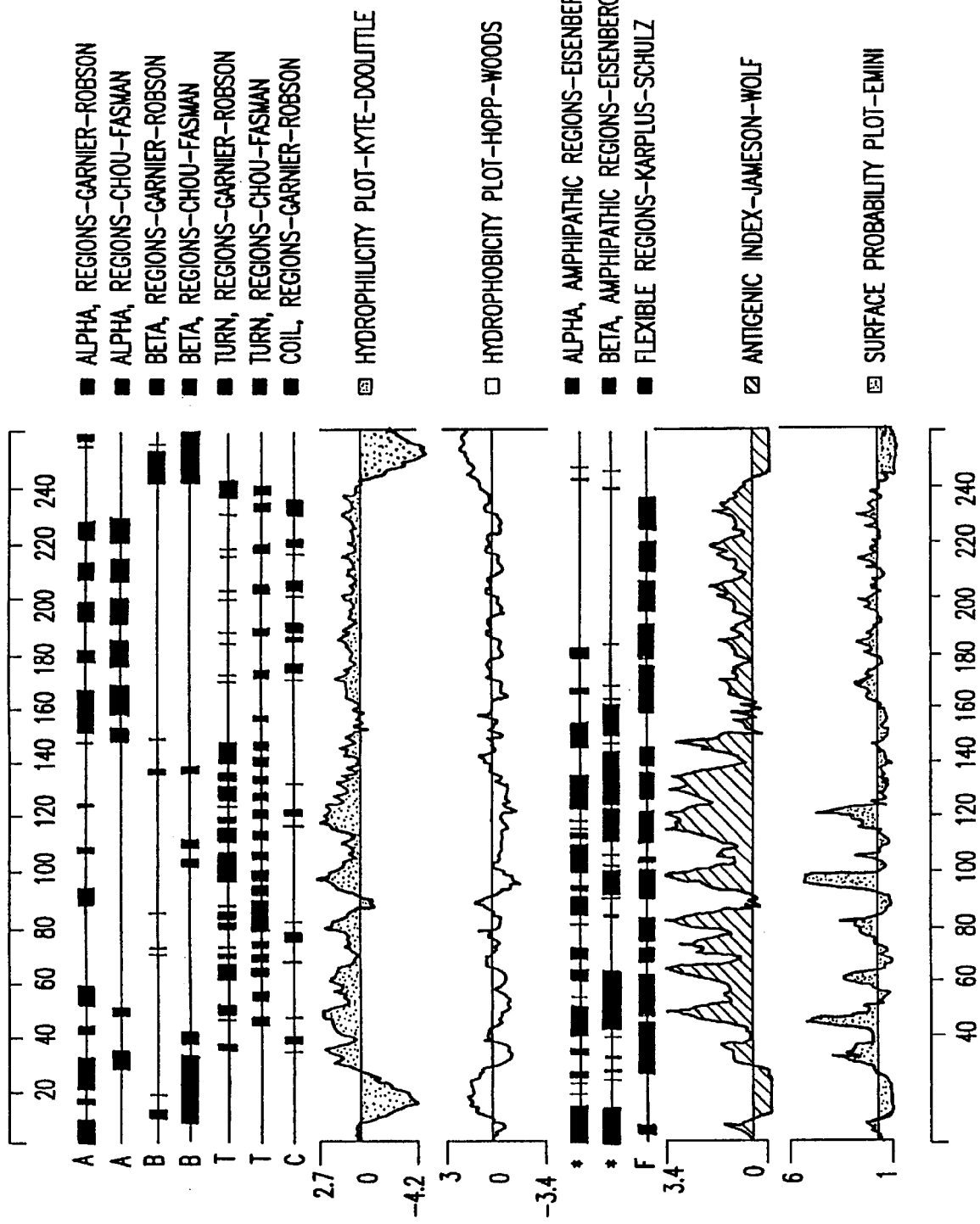
FIG. 3 shows an analyses of the TRID amino acid sequences. Alpha, beta, turn and coil regions; hydrophilicity and hydrophobicity; amphipathic regions; flexible regions; antigenic index and surface probability are shown. In the "Antigenic Index—Jameson-Wolf" graphs, the indicate location of the highly antigenic regions of the proteins, i.e., regions from which epitope-bearing peptides of the invention may be obtained.

The present invention provides isolated nucleic acid molecules comprising a polynucleotide encoding a TRID polypeptide, having the amino acid sequence shown in SEQ ID NO:2, which was determined by sequencing a cloned cDNA. The nucleotide sequence shown in SEQ ID NO:1 was obtained by sequencing the HPRCB54 clone, which was deposited on Nov. 20, 1996 at the American Type Culture Collection, patent depository, 10801 University Boulevard, Manassas, Va. 20110-2209, and given accession number 97798. The deposited clone is inserted in the pBluescript SK(-) plasmid (Stratagene, La Jolla, Calif.).

Figure 2A:
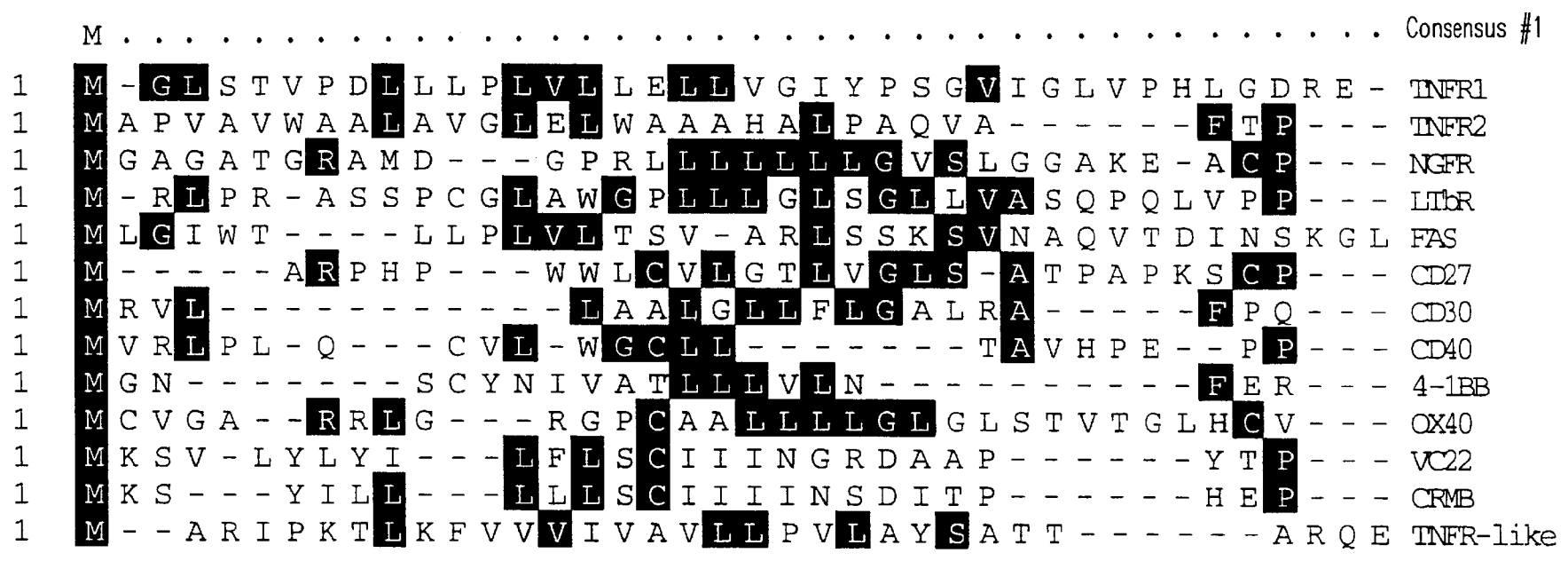
Figure 2B:
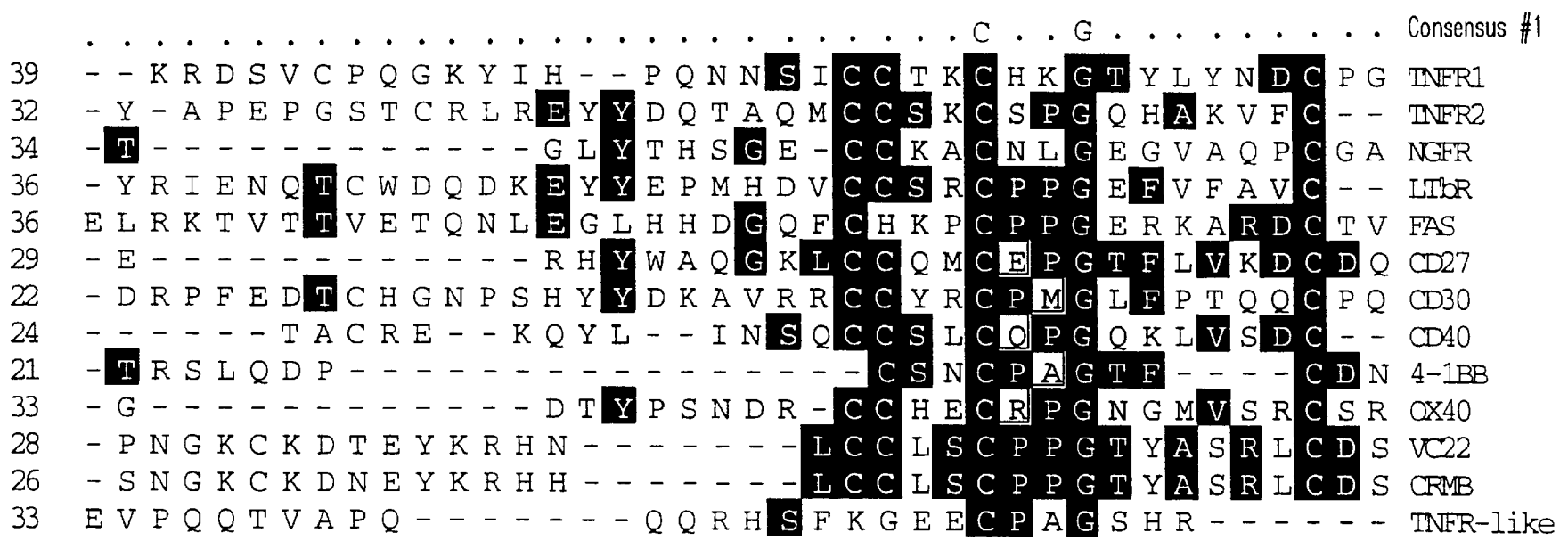
Figure 2C:
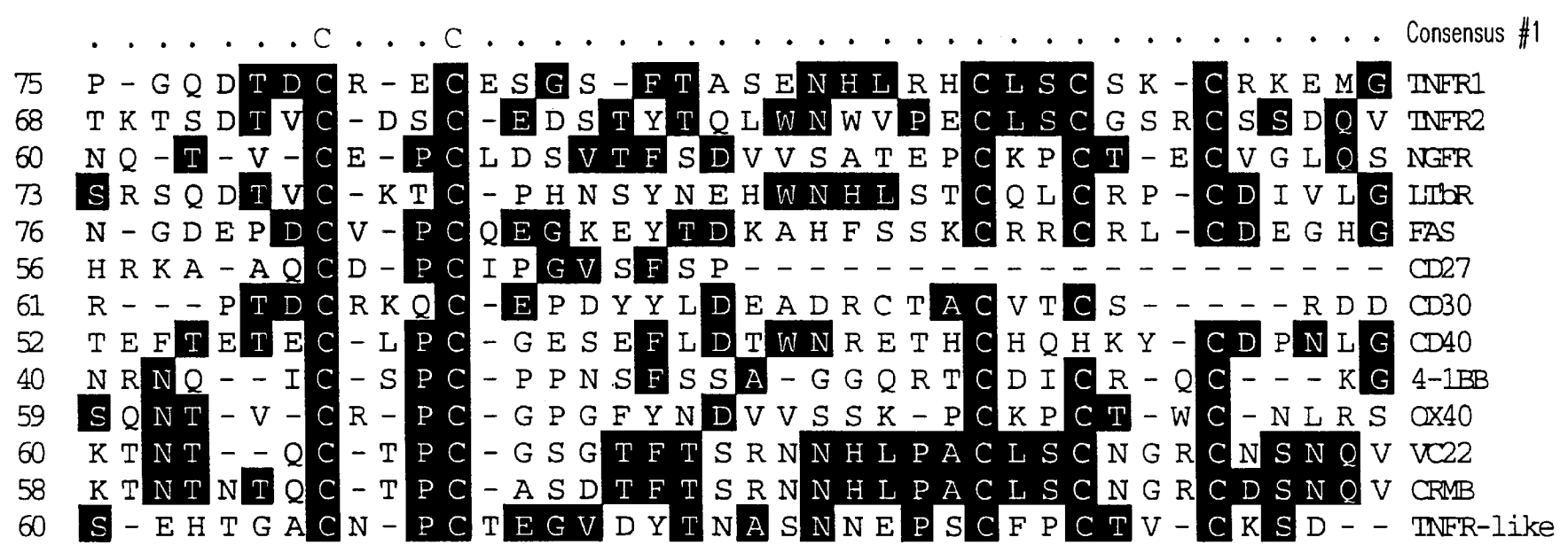
Figure 2D:
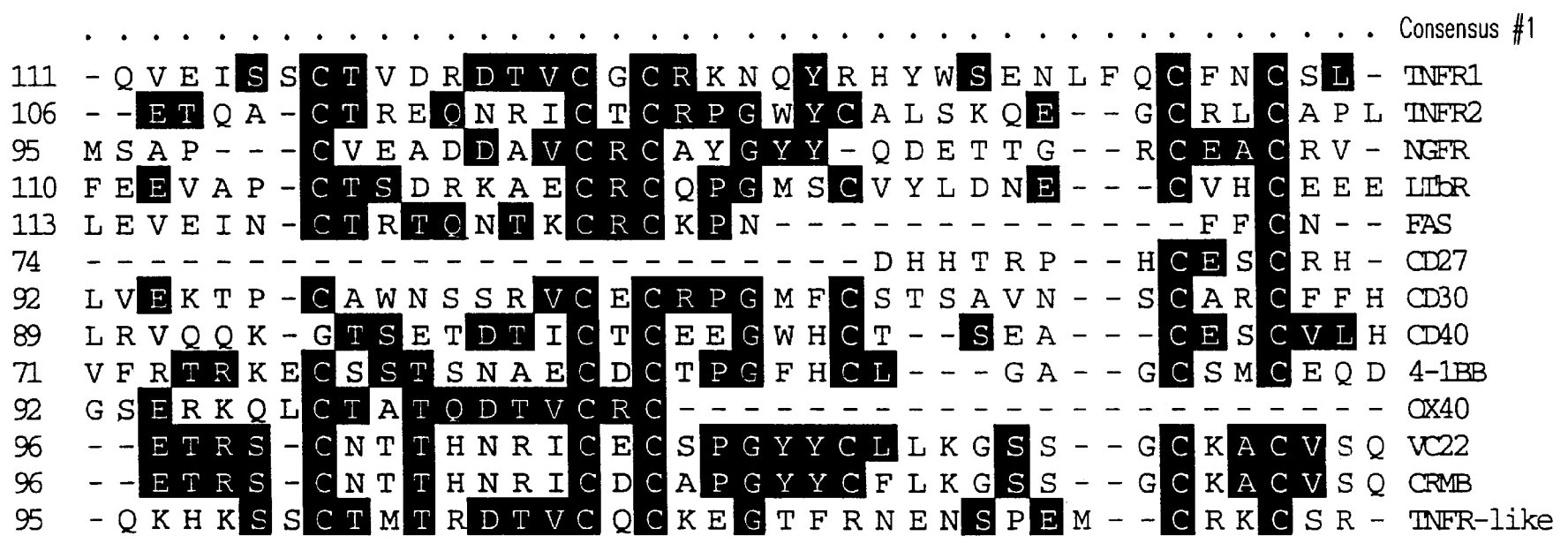
Figure 2E:
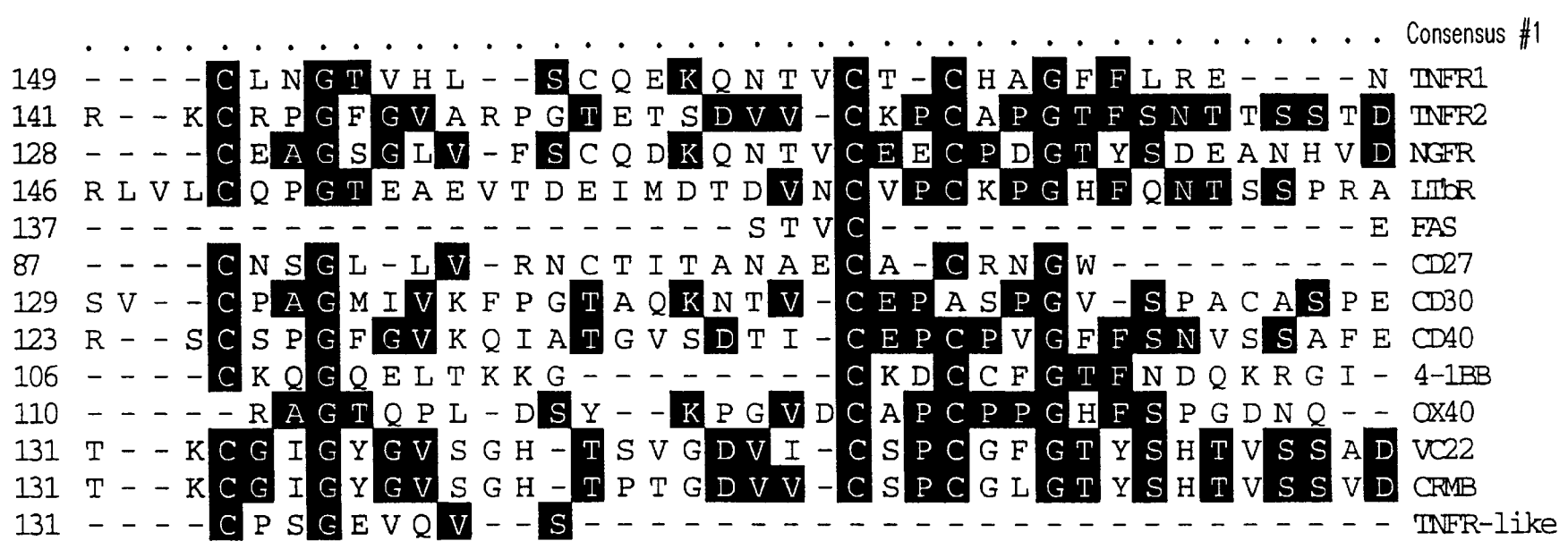
Figure 2F:
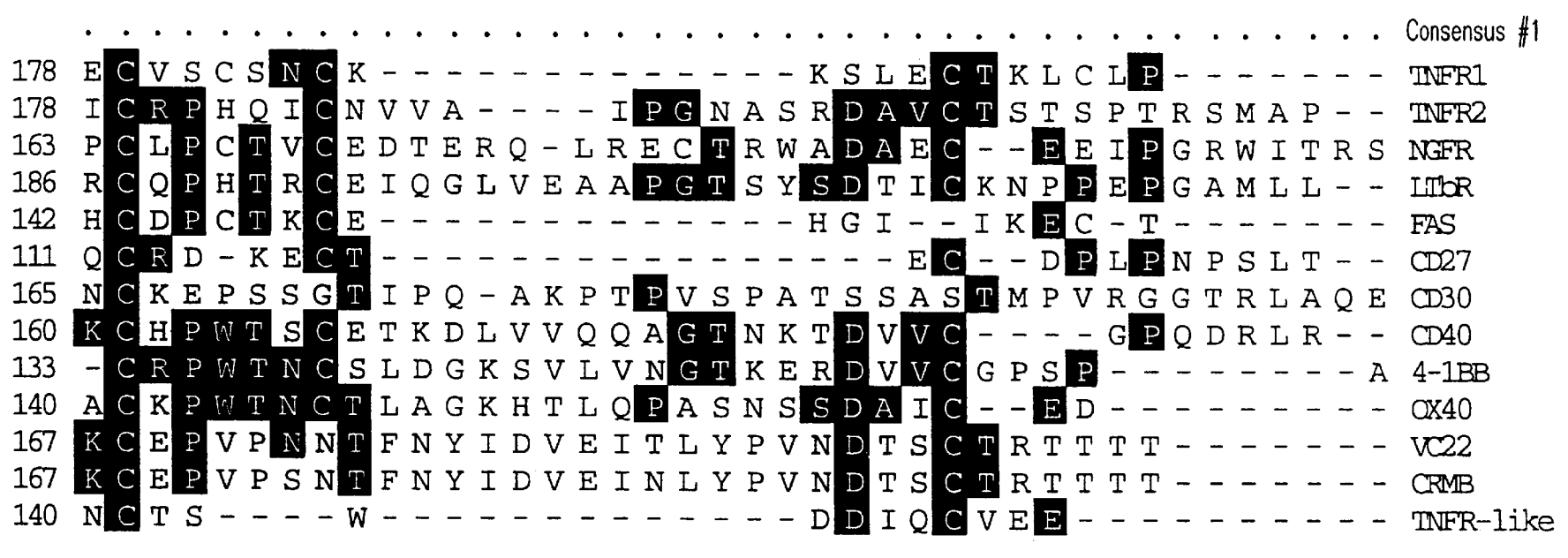
Figure 2J:
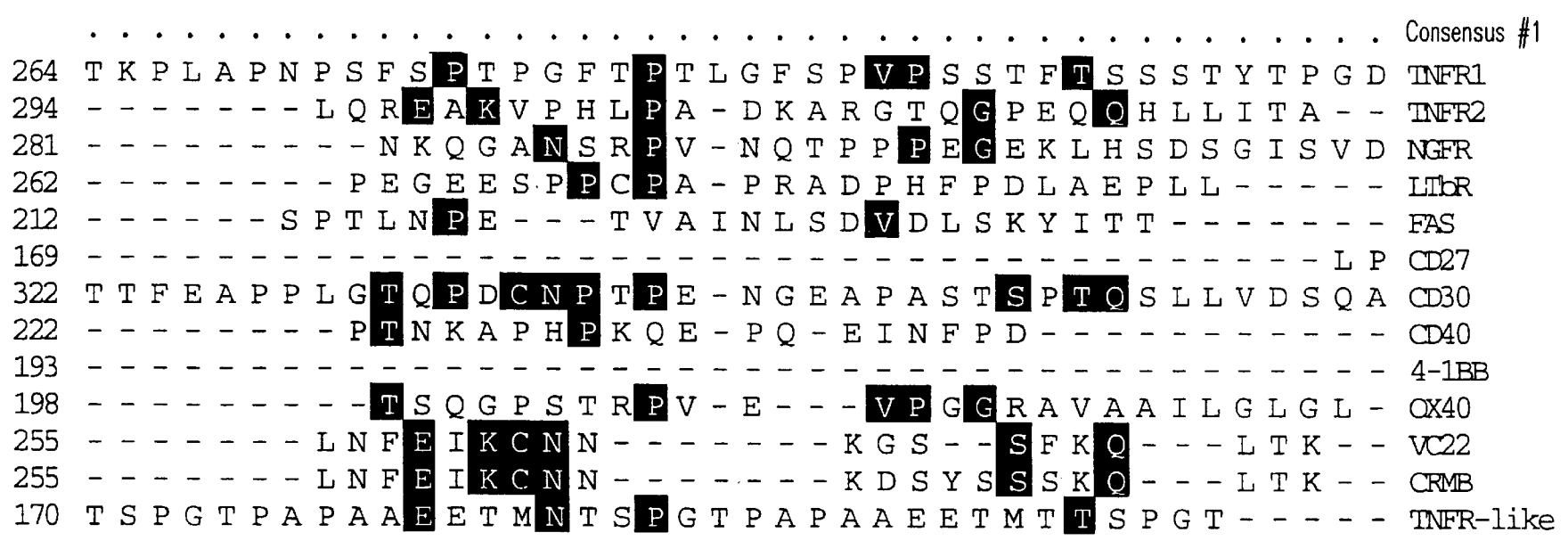
Figure 2M:
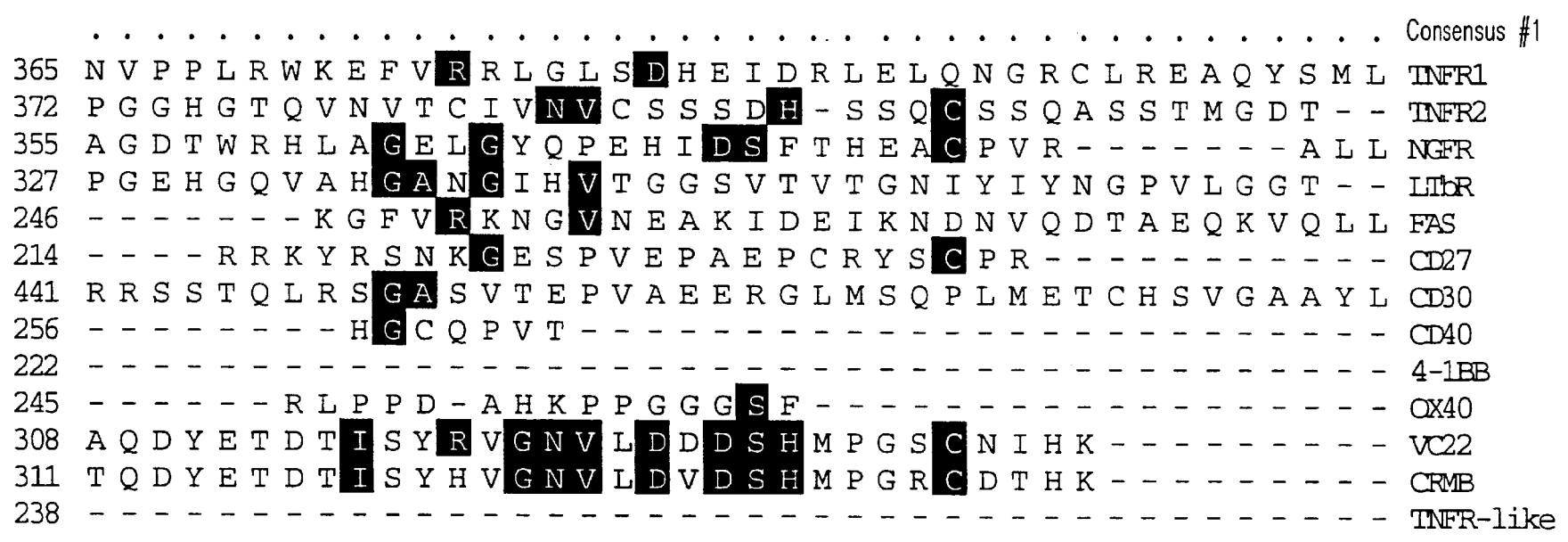

The TRID protein of the present invention has an amino acid sequence which is 21.7% identical to and shares multiple conserved cysteine rich domains with the translation product of the human nerve growth factor (hNGF) mRNA (SEQ ID NO:5) as illustrated in FIGS. 2A–2P. hNGF is thought to play an important role in the development, survival, apoptosis and function of neurons (Lee, F. K., et al., Cell 69:737) and lymphocytes (Torcia, M. et al., Cell 85:3369 (1996)).

Sequence alignment and comparison reveal that TRID's extracellular cysteine-rich domain to be strikingly similar to the corresponding domains of both DR4 and DR5 with 69% and 52% amino acid identity, respectively. In addition, like DR4 and DR5, TRID was also found to be homologous to the cysteine-rich domain in CAR1, a chicken TNF receptor family member with amino acid identities ranging from 42–48% (J. Brojatsh et al., Cell 87:1(1996)). A potential protective role for TRID was suggested by the finding that its transcript was detectable in many normal human tissues but not in most transformed cell lines.

TRID has an extracellular TRAIL binding domain and a transmembrane domain but, surprisingly, lacks a putative intracellular signalling domain, in keeping with the possibility that this receptor does not signal following ligand binding. Given the absence of an intracellular domain, this receptor was termed "TRID" for TRAIL Receptor Without an Intracellular Domain.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence set out in SEQ ID NO:1, a nucleic acid molecule of the present invention encoding a TRID polypeptide may be obtained using standard cloning and screening procedures, such as those for cloning cDNAs using mRNA as starting material. Illustrative of the invention, the TRID nucleic acid molecule described in SEQ ID NO:1 was discovered in a cDNA library derived from prostate tissue. Additional clones of the same gene were also identified in cDNA libraries from the following tissues: endothelial cells, stimulated monocytes, and kerotinocytes.

The determined nucleotide sequence of the TRID cDNA of SEQ ID NO:1 contains an open reading frame encoding a protein of about 259 amino acid residues, with an initiation codon at nucleotide positions 183–185 of the nucleotide sequences in SEQ ID NO:1.

The open reading frame of the TRID gene shares sequence homology with the translation product of the human mRNA for NGFR, including the following conserved domains: (a) a soluble extracellular domain of about 214 amino acids (residues 1–214 of SEQ ID NO:2); and (b) a transmembrane domain of about 19 amino acids (residues 215–233 of SEQ ID NO:2).

As one of ordinary skill would appreciate, due to the possibility of sequencing errors discussed above, the actual complete TRID polypeptide encoded by the deposited cDNAs, which comprise about 259 amino acids, may be somewhat longer or shorter. More generally, the actual open reading frames may be anywhere in the range of ±20 amino acids, more likely in the range of ±10 amino acids, of that predicted from the first methionine codon from the N-terminus shown in SEQ ID NO:1, which is in-frame with the translated sequences shown in each respective figure. It will further be appreciated that, depending on the analytical criteria used for identifying various functional domains, the exact "address" of the extracellular and transmembrane domain(s) of the TNFR polypeptides may differ slightly from the predicted positions above. For example, the exact location of the extracellular domain in SEQ ID NO:2 may vary slightly (e.g., the address may "shift" by about 1 to about 20 residues, more likely about 1 to about 5 residues) depending on the criteria used to define the domain. In this case, the beginning of the transmembrane domain and the end of the extracellular domain were predicted on the basis of the identification of the hydrophobic amino acid sequence in the above indicated positions, as shown in FIG. 3. In any event, as discussed further below, the invention further provides polypeptides having various residues deleted from the N-terminus of the complete polypeptide, including polypeptides lacking one or more amino acids from the N-terminus of the extracellular domain described herein, which constitute soluble forms of the extracellular domain of the TRID protein.

Leader and Mature Sequences

The amino acid sequence of the TRID protein includes a leader sequence and a mature protein, as shown in SEQ ID NO:2. More in particular, the present invention provides nucleic acid molecules encoding mature forms of the TRID protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding a mature TRID polypeptide having the amino acid sequence encoded by a cDNA clone identified as ATCC Deposit No. 97798. By the "mature TRID polypeptide having the amino acid sequence encoded by a cDNA clone in ATCC Deposit No. 97798" is meant the mature form(s) of the protein produced by expression in a mammalian cell (e.g., COS cells, as described below) of the complete open reading frame encoded by the human DNA sequence of the clone contained in the deposited plasmid.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete TRID polypeptide was analyzed by a computerprogram "PSORT." See, K. Nakai and M. Kanehisa, *Genomics* 14:897–911 (1992). PSORT is an expert system for predicting the cellular location of a protein based on the amino acid sequence. As part of this computational prediction of localization, the methods of McGeoch and von Heinje are incorporated. The analysis by the PSORT program predicted the cleavage sites between amino acids −1 and 1 in SEQ ID NO:2. Thereafter, the complete amino acid sequences were further analyzed by visual inspection, applying asimple formof the (−1, −3) rule of von Heinje. von Heinje, supra. Thus, the leader sequence for the TRID protein is predicted to consist of amino acid residues from about −26 to about −1 in SEQ ID NO:2, while the mature TRID protein is predicted to consist of residues from about 1 to about 233 in SEQ ID NO:2.

As one of ordinary skill would appreciate, due to the possibilities of sequencing errors, as well as the variability of cleavage sites for leaders in different known proteins, the mature TRID polypeptide encoded by the deposited cDNA comprises about 233 amino acids, but may be anywhere in the range of about 223 to about 243 amino acids, and the predicted leader sequence of this protein is about 26 amino acids, but may be anywhere in the range of about 16 to about 36 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA, or RNA, which has been removed from its native environment. For example, recombinant DNA molecules contained in a vector are considered isolated for the purposes of the present invention. Further examples of isolated DNA molecules include recombinant DNA molecules maintained inheterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in SEQ ID NO:1; DNA molecules comprising the coding sequence for the mature TRID protein; and DNA molecules which comprise a sequence substantially different from those described above, but which, due to the degeneracy of the genetic code, still encode the TRID protein. Of course, the genetic code is well known in the art. Thus, it would be routine for one skilled in the art to generate such degenerate variants.

In addition, the invention provides nucleic acid molecules having nucleotide sequences related to extensive portions of SEQ ID NO:1, which have been determined from the following related cDNA clones: HELBP70R (SEQ ID NO:17), HPRCB54R (SEQ ID NO:15), HSJAU57RA (SEQ ID NO:16) and HUSCB54R (SEQ ID NO:18). The nucleotide sequences of each of these gene fragments is shown in FIG. 4.

In another aspect, the invention provides isolated nucleic acid molecules encoding the TRID polypeptide having an amino acid sequence as encoded by the cDNA clone contained in the plasmid deposited as ATCC Deposit No. 97798. In a further embodiment, nucleic acid molecules are provided that encode the mature TRID polypeptide or the full length TRID polypeptide each lacking the N-terminal methionine.

The invention further provides an isolated nucleic acid molecule having the nucleotide sequence shown in SEQ ID NO:1 or the nucleotide sequence of the TRID cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the TRID gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt, or even 600 nt in length are also useful according to the present invention as are fragments corresponding to most, if not all, of the nucleotide sequence of the deposited cDNA or as shown in SEQ ID NO:1. By a fragment at least 20 nt in length, for example, is intended fragments which include 20 or more contiguous bases from the nucleotide sequence of a deposited cDNA or the nucleotide sequence as shown in SEQ ID NO:1.

Preferred nucleic acid fragments of the present invention include nucleic acid molecules encoding: epitope-bearing portions of the TRID polypeptide as identified in FIG. 3 and described in more detail below.

In particular, the invention provides polynucleotides having a nucleotide sequence representing the portion of SEQ ID NO:1, which consist of positions 183 to 959 of SEQ ID NO:1. Also contemplated are polynucleotides encoding TRID polypeptides which lack an amino terminal methionine. One such preferred polynucleotide has a nucleotide sequence representing the portion of SEQ ID NO:1 which consists of positions 186 to 959. Polypeptides encoded by such polynucleotides are also provided, such polypeptides comprising an amino acid sequence at positions −25 to 233 of SEQ ID NO:2, or the polypeptide sequence encoded by the clone deposited with the ATCC as Deposit No. 97798 lacking an amino terminal methionine.

Preferred nucleic acid fragments of the present invention include nucleic acid molecules encoding: a polypeptide comprising the TRID extracellular domain (amino acid residues from about 1 to about 214 in SEQ ID NO:2); and a polypeptide comprising the TRID transmembrane domain (amino acid residues from about 215 to about 233 in SEQ ID NO:2). Since the location of these domains have been predicted by computer graphics, one of ordinary skill would appreciate that the amino acid residues constituting these domains may vary slightly (e.g., by about 1 to 15 residues) depending on the criteria used to define each domain.

Preferred nucleic acid fragments of the invention encode a full-length TRID polypeptide lacking the nucleotides encoding the amino-terminal methionine (e.g., nucleotides 186 to 959 in SEQ ID NO:1) as it is known that the methionine is cleaved naturally and such sequences maybe useful in genetically engineering TRID expression vectors. Polypeptides encoded by such polynucleotides are also contemplated by the invention.

Preferred nucleic acid fragments of the present invention further include nucleic acid molecules encoding epitope-bearing portions of the TRID protein. In particular, such nucleic acid fragments of the present invention include nucleic acid molecules encoding: a polypeptide comprising amino acid residues from about Gln-16 to about Glu-26 in SEQ ID NO:2; a polypeptide comprising amino acid residues from about His-32 to about Cys-40 in SEQ ID NO:2; apolypeptide comprising amino acid residues from about Pro-42 to about Thr-50 in SEQ ID NO:2; a polypeptide comprising amino acid residues from about Ser-53 to about Cys-59 in SEQ ID NO:2; a polypeptide comprising amino acid residues from about Cys-65 to about Thr-76 in SEQ ID NO:2; a polypeptide comprising amino acid residues from about Gln-84 to about Pro-96 in SEQ ID NO:2; apolypeptide comprising amino acid residues from about Arg-100 to about Val-110 in SEQ ID NO:2; and a polypeptide comprising amino acid residues from about Thr-116 to about Gln-122 in SEQ ID NO:2. The inventors have determined that the above polypeptide fragments are antigenic regions of the TRID protein. Methods for determining other such epitope-bearing portions of the TRID protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, a cDNA clone contained in ATCC DepositNo.97798. By "stringent hybridization conditions" is intended overnight incubation at 42° C. in a solution comprising:50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., a deposited cDNA or the nucleotide sequence as shown in SEQ ID NO:1). Of course, a polynucleotide which hybridizes only to a poly A sequence (such as the 3' terminal poly(A) tract of the TRID cDNA shown in SEQ ID NO:1), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a TRID polypeptide may include, but are not limited to the coding sequence for the mature polypeptide, by itself, the coding sequence for the mature polypeptide and additional sequences, such as those encoding a leader or secretary sequence, such as a pre-, or pro- or pre-proprotein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778(1984). As discussed below, other such fusion proteins include the TRID receptor fused to Fc at the N- or C-terminus.

Variant and Mutant Polynucleotides

The present invention further relates to variants of the nucleic acid molecules of the present invention, which encode portions, analogs, or derivatives of the TRID receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TRID polypeptide or portions thereof. Also especially preferred in this regard are conservative substitutions.

Further embodiments of the invention include an isolated nucleic acid molecule comprising a polynucleotide having a nucleotide sequence at least 90% identical, and more preferably at least 95%, 96%, 97%, 98% or 99% identical to: (a) a nucleotide sequence encoding the polypeptide having the amino acid sequence in SEQ ID NO:2; (b) a nucleotide sequence encoding the polypeptide having the amino acid sequence in SEQ ID NO:2, but lacking the amino terminal methionine; (c) a nucleotide sequence encoding the polypeptide having the amino acid sequence at positions about 1 to about 233 in SEQ ID NO:2; (d) a nucleotide sequence encoding the polypeptide having the amino acid sequence encoded by the cDNA clone contained in ATCC Deposit No. 97798; (e) a nucleotide sequence encoding the mature TRID polypeptide having the amino acid sequence encoded by the cDNA clone contained in ATCC Deposit No. 97798; (f) a nucleotide sequence that encodes the TRID extracellular domain having the amino acid sequence at positions about 1 to about 214 in SEQ ID NO:2, or the TRID extracellular domain encoded by the cDNA contained in ATCC Deposit No. 97798; (g) a nucleotide sequence that encodes the TRID transmembrane domain having the amino acid sequence at positions about 215 to about 233 of SEQ ID NO:2, or the TRID transmembrane domain encoded by the cDNA contained in ATCC Deposit No. 97798; and (h) a nucleotide sequence complementary to any of the nucleotide sequences in (a), (b), (c), (d), (e), (f), or (g) above.

Further embodiments of the invention include isolated nucleic acid molecules that comprise a polynucleotide which hybridizes under stringent hybridization conditions to a polynucleotide in (a), (b), (c), (d), (e), (f), (g) or (h) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a TRID polypeptide having an amino acid sequence in (a), (b), (c), (d), (e), (f) or (g) above.

By a polynucleotide having a nucleotide sequence at least, for example, 95% "identical" to a reference nucleotide sequence encoding a TRID polypeptide is intended that the nucleotide sequence of the polynucleotide is identical to the reference sequence except that the polynucleotide sequence may include up to five point mutations per each 100 nucleotides of the reference nucleotide sequence encoding the TRID polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in SEQ ID NO:1, or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to a nucleic acid sequence shown in SEQ ID NO:1, or to the nucleic acid sequence of the deposited cDNA, irrespective of whether they encode a polypeptide having TRID activity. This is because even where a particular nucleic acid molecule does not encode a polypeptide having TRID activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TRID activity include, inter alia: (1) isolating a TRID gene or allelic variants thereof in a cDNA library; (2) in situ hybridization (e.g., "FISH") to metaphase chromosomal spreads to provide precise chromosomal location of the TRID gene, as described in Verma et al., Human Chromosomes: A Manual of Basic Techniques, Pergamon Press, New York (1988); and Northern Blot analysis for detecting TRID mRNA expression in specific tissues.

Preferred, however, are nucleic acid molecules having sequences at least 90%, 95%, 96%, 97%, 98% or 99% identical to a nucleic acid sequence shown in SEQ ID NO:1, or to the nucleic acid sequence of the deposited cDNA which does, in fact, encode a polypeptide having TRID receptor activity. By "a polypeptide having TRID receptor activity" is intended polypeptides exhibiting activity similar, but not necessarily identical, to an activity of the TRID receptor of the invention (either the full length protein or preferably the mature protein or extracellular domain alone), as measured in a particular biological assay. The TNF family ligands (including TRAIL) induce various cellular responses by binding to TNF-family receptors, including the TRID of the present invention. Cells which express TRID are believed to have a potent cellular response to ligands including TRAIL. By a "cellular response to a TNF-family ligand" is intended any genotypic, phenotypic, and/or morphological change to a cell, cell line, tissue, tissue culture or patient that is induced by a TNF-family ligand. As indicated, such cellular responses include not only normal physiological responses to TNF-family ligands, but also diseases associated with increased cell proliferation or the inhibition of increased cell proliferation, such as by the inhibition of apoptosis.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of a deposited cDNA or the nucleic acid sequence shown in SEQ ID NO:1 will encode apolypeptide "having TRID protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TRID protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors of the invention and the production of TRID polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH 16a, pNH 18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses, it would be desirable to be able to delete the Fc part after the fusion protein has been expressed, detected and purified in the advantageous manner described. This is the case when the Fc portion proves to be a hindrance to use in therapy and diagnosis, for example, when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *Journal of Molecular Recognition* 8:52–58 (1995) and K. Johanson et al., *The Journal of Biological Chemistry* 270:16:9459–9471 (1995).

The TRID receptor can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may also include an initial modified methionine residue, in some cases as a result of host-mediated processes.

TRID receptor polynucleotides and polypeptides may be used in accordance with the present invention for a variety of applications, particularly those that make use of the chemical and biological properties of TRID. Among these are applications in treatment of tumors, resistance to parasites, bacteria and viruses, to induce proliferation of T-cells, endothelial cells and certain hematopoietic cells, to treat restenosis, graft vs. host disease, to regulate anti-viral responses and to prevent certain autoimmune diseases after stimulation of TRID by an agonist. Additional applications relate to diagnosis and to treatment of disorders of cells, tissues and organisms. These aspects of the invention are discussed further below.

Polypeptides and Fragments

The invention further provides an isolated TRID polypeptide having the amino acid sequences encoded by the deposited cDNA, or the amino acid sequences in SEQ ID NO:2, or a peptide or polypeptide comprising a portion of the above polypeptides.

Variant and Mutant Polypeptides

To improve or alter the characteristics of a TRID polypeptide, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing. In the present case, since the proteins of the invention are members of the TNFR polypeptide family, deletions of N-terminal amino acids up to the cysteine at position C-27 of SEQ ID NO:2 may retain some biological activity such as regulation of proliferation and apoptosis of lymphoid cells. Polypeptides having further N-terminal deletions including the C-27 in SEQ ID NO:2, would not be expected to retain such biological activities because it is known that these residues in a TRID-related polypeptide are required for forming a disulfide bridge to provide structural stability which is needed for ligand binding.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or mature form of the TRID protein generally will be retained when less than the majority of the residues of the complete protein or extracellular domain are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence shown in SEQ ID NO:2, up to the cysteine residue which is at position number 27, and polynucleotides encoding such polypeptides. In particular, the present invention provides TRID polypeptides comprising the amino acid sequence of residues m to 233 of SEQ ID NO:2 where m is an integer in the range of −26 to 27 where 27 is the position of the first cysteine residue from the N-terminus of the complete TRID polypeptide (shown in SEQ ID NO:2) believed to be required for activity of the TRID protein.

More in particular, the invention provides polynucleotides encoding polypeptides having the amino acid sequence of residues: −26 to 233, −25 to 233, −24 to 233, −23 to 233, −22 to 233, −21 to 233, −20 to 233, −19 to 233, −18 to 233, −17 to 233, −16 to 233, −15 to 233, −14 to 233, −13 to 233, −12 to 233, −11 to 233, −10 to 233, −9 to 233, −8 to 233, −7 to 233, −6 to 233, −5 to 233, −4 to 233, −3 to 233, −2 to 233, −1 to 233, 1 to 233, 2 to 233, 3 to 233, 4 to 233, 5 to 233, 6 to 233, 7 to 233, 8 to 233, 9 to 233, 10 to 233, 11 to 233, 12 to 233, 13 to 233, 14 to 233, 15 to 233, 16 to 233, 17 to 233, 18 to 233, 19 to 233, 20 to 233, 21 to 233, 22 to 233, 23 to 233, 24 to 233, 25 to 233, 26 to 233, and 27 to 233 of SEQ ID NO:2. Polynucleotides encoding these polypeptides also are provided.

Similarly, many examples of biologically functional C-terminal deletion muteins are known. For instance, interferon gamma shows up to ten times higher activities by deleting 8 to 10 amino acid residues from the carboxy terminus of the protein (Döbeli et al., *J. Biotechnology* 7:199–216 (1988)). In the present case, since the protein of the invention is a member of the TNFR polypeptide family, deletions of C-terminal amino acids up to the cysteine at position 123 of SEQ ID NO:2, may retain some biological activity such as regulation of proliferation and apoptosis of lymphoid cells. Polypeptides having further C-terminal deletions including the cysteine at position 123 of SEQ ID NO:2 would not be expected to retain such biological activities because it is known that this residue in TNF receptor-related polypeptides is required for forming a disulfide bridge to provide structural stability which is needed for ligand binding.

However, even if deletion of one or more amino acids from the C-terminus of a protein results in modification or loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature form protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of TRID shown in SEQ ID NO:2 up to the cysteine at position 123 of SEQ ID NO:2, and polynucleotides encoding such polypeptides. In particular, the present invention provides polypeptides having the amino acid sequence of residues −26 to x of the amino acid sequence in SEQ ID NO:2, where x is any integer in the range of 123 to 233. Polynucleotides encoding these polypeptides also are provided.

The invention also provides polypeptides having one or more amino acids deleted from both the amino and the carboxyl termini, which may be described generally as having residues m to x of SEQ ID NO:2, where m and x are integers as described above.

In a specific embodiment, the invention encompasses an isolated nucleic acid molecule comprising a polynucleotide having a nucleotide sequence at least 95% identical to a sequence selected from the group consisting of: (a) a nucleotide sequence encoding a polypeptide comprising the amino acid sequence of residues m to 233 of SEQ ID NO:2, where m is an integer in the range of −26 to 27; (b) a nucleotide sequence encoding a polypeptide comprising the amino acid sequence of residues 1 to x of SEQ ID NO:2, where x is n integer in the range of 123 to 233; and (c) a nucleotide sequence encoding a polypeptide having the amino acid sequence consisting of residues m to x of SEQ ID NO:2, m and x are defined in (a) and (b) above.

Also included are a nucleotide sequence encoding a polypeptide consisting of a portion of a complete TRID amino acid sequence encoded by a cDNA clone contained in ATCC Deposit No. 97798, where this portion excludes from 1 to about 49 amino acids from the amino terminus of the complete amino acid sequence encoded by the cDNA clone contained in ATCC Deposit No. 97798, or from 1 to about 110 amino acids from the carboxy terminus of the complete amino acid sequence encoded by the cDNA clone contained in ATCC Deposit No. 97798, or any combination of the above amino terminal and carboxy terminal deletions, of the complete amino acid sequence encoded by the cDNA clone contained in ATCC Deposit No. 97798. Polynucleotides encoding all of the above deletion mutant polypeptide forms also are provided.

Other Mutants

In addition to terminal deletion forms of the protein discussed above, it will also be recognized by one of ordinary skill in the art that some amino acid sequences of the TRID polypeptide can be varied without significant effect on the structure or function of the proteins. If such differences in sequence are contemplated, it should be remembered that there will be critical areas on the protein which determine activity. Thus, the invention further includes variations of the TRID polypeptide, which show substantial TRID polypeptide activity or which include regions of TRID protein such as the protein portions discussed below. Such mutants include deletions, insertions, inversions, repeats, and type substitutions Guidance concerning which amino acid changes are likely to be phenotypically silent can be found in Bowie, J. U. et al., "Deciphering the Message in Protein Sequences: Tolerance to Amino Acid Substitutions," Science 247:1306–1310 (1990).

Thus, the fragment, derivative, or analog of the polypeptide of SEQ ID NO:2, or that encoded by the deposited cDNA, may be: (i) one in which one or more of the amino acid residues are substituted with a conserved or non-conserved amino acid residue (preferably a conserved amino acid residue(s), and more preferably at least one but less than ten conserved amino acid residue(s)), and such substituted amino acid residue(s) may or may not be one encoded by the genetic code; or (ii) one in which one or more of the amino acid residues includes a substituent group;or (iii) one in which the mature or soluble extracellular polypeptide is fused with another compound, such as a compound to increase the half-life of the polypeptide (for example, polyethylene glycol); or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Thus, the TRID of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

| Conservative Amino Acid Substitutions | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TRID protein of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding or in vitro proliferative activity.

Of particular interest are substitutions of charged amino acids with another charged amino acids and with neutral or negatively charged amino acids. The latter results in proteins with reduced positive charge to improve the characteristics of the TRID protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding of a ligand to cell surface receptors. For example, Ostade et al., *Nature* 361:266–268 (1993), describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904(1992) and de Vos et al. *Science* 255:306–312 (1992)).

The polypeptides of the present invention are preferably provided in an isolated form. By "isolated polypeptide" is intended a polypeptide removed from its native environment. The a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the TRID polypeptide can be substantially purified by the one-step method described in Smith and Johnson, *Gene* 67:31–40 (1988).

The present inventors have discovered that the TRID polypeptide is a 259 residue protein exhibiting two main structural domains. First, the extracellular TRAIL ligand binding domain was identified within residues from about 1 to about 214 in SEQ ID NO:2. Second, the transmembrane domain was identified within residues from about 215 to about 233 in SEQ ID NO:2. As mentioned above, however, TRID, surprisingly lacks a putative intracellular signalling domain, thus, the name "TRID" (TRAIL Receptor Without an Intracellular Domain").

The polypeptides of the present invention include the polypeptide encoded by the deposited cDNA including the leader; the mature polypeptide encoded by the deposited the cDNA minus the leader (i.e., the mature protein); a polypeptide comprising amino acids about −26 to about 233 in SEQ ID NO:2; a polypeptide comprising amino acids about −25 to about 233 in SEQ ID NO:2; a polypeptide comprising amino acids about 1 to about 233 in SEQ ID NO:2; a polypeptide comprising the extracellular domain; and a polypeptide comprising the transmembrane domain; as well as polypeptides which are at least 80% identical, more preferably at least 90% or 95% identical, still more preferably at least 96%, 97%,98%, or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a TRID polypeptide is intended that the amino acid sequence of the polypeptide is identical to the reference sequence except that the polypeptide sequence may include up to five amino acid alterations per each 100 amino acids of the reference amino acid of the TRID polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2, or to the amino acid sequence encoded by the deposited cDNA clone, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies That React With Predetermined Sites on Proteins," *Science,* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention.

Non-limiting examples of antigenic polypeptides or peptides that can be used to generate TRID-specific antibodies include: a polypeptide comprising amino acid residues from about Gln-16 to about Glu-26 in SEQ ID NO:2; a polypeptide comprising amino acid residues from about His-32 to about Cys-40 in SEQ ID NO:2; a polypeptide comprising amino acid residues from about Pro-42 to about Thr-50 in SEQ ID NO:2; a polypeptide comprising amino acid residues from about Ser-53 to about Cys-59 in SEQ ID NO:2; a polypeptide comprising amino acid residues from about Cys-65 to about Thr-76 in SEQ ID NO:2; a polypeptide comprising amino acid residues from about Gln-84 to about Pro-96 in SEQ ID NO:2; a polypeptide comprising amino acid residues from about Arg-100 to about Val-110 in SEQ ID NO:2; and a polypeptide comprising amino acid residues from about Thr-116 to about Gln-122 in SEQ ID NO:2. As indicated above, the inventors have determined that the above polypeptide fragments are antigenic regions of the TRID protein.

The epitope-bearing peptides and polypeptides of the invention may be produced by any conventional means See, e.g., Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131–5135; this "Simultaneous Multiple Peptide Synthesis (SMPS)" process is further described in U.S. Pat. No. 4,631,211 to Houghten et al., (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is atopographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, TRID receptor polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric TRID protein or protein fragment alone (Fountoulakis et al., *J. Biochem.* 270:3958–3964 (1995)).

Antibodies

TRID-protein specific antibodies for use in the present invention can be raised against the intact TRIDproteins or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to a TNFR protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the TRID protein or an antigenic fragment thereof can be administered to an animal in order to induce the production of sera containing polyclonal antibodies. In a preferred method, a preparation of TRID protein is prepared and purified to render it substantially free of natural contaminants. Such a preparation is then introduced into an animal in order to produce polyclonal antisera of greater specific activity.

In the most preferred method, the antibodies of the present invention are monoclonal antibodies. Such monoclonal antibodies can be prepared using hybridoma technology (Köhler et al., *Nature* 256:495 (1975); Köhler et al., *Eur. J. Immunol.* 6:511 (1976); Köhler et al., Eur. J. Immunol. 6:292 (1976); Hammerling et al., in: *Monoclonal Antibodies and T-Cell Hybridomas,* Elsevier, N.Y., (1981) pp. 563–681 ). In general, such procedures involve immunizing an animal (preferably a mouse) with a TRID protein antigen or, more preferably, with a TRID protein-expressing cell. Suitable cells can be recognized by their capacity to bind anti-TRID protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the American Type Culture Collection, Manassas, Va. After fusion, the resulting hybridoma cells are selectively maintained in HAT medium, and then cloned by limiting dilution as described by Wands et al., (Gastroenterology 80:225–232 (1981)). The hybridoma cells obtained through such a selection are then assayed to identify clones which secrete antibodies capable of binding the desired TRID antigen.

Alternatively, additional antibodies capable of binding to the TRID antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, TRID-protein specific antibodies are used to immunize an animal, preferably a mouse. The splenocytes of such an animal are then used to produce hybridoma cells, and the hybridoma cells are screened to identify clones which produce an antibody whose ability to bind to the TRID protein-specific antibody can be blocked by the TRID protein antigen. Such antibodies comprise anti-idiotypic antibodies to the TRID protein-specific antibody and can be used to immunize an animal to induce formation of further TRID protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, TRID protein-binding fragments can be produced through the application of recombinant DNA technology or through synthetic chemistry.

For in vivo use of anti-TRID in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214(1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Immune System-Related Disorders

Diagnosis

The present inventors have discovered that TRID is expressed in hematopoeitic tissues and other normal human tissues. For a number of immune system-related disorders, substantially altered (increased or decreased) levels of TRID gene expression can be detected in immune system tissue or other cells or bodily fluids (e.g., sera and plasma) taken from an individual having such a disorder, relative to a "standard" TRID gene expression level, that is, the TRID expression level in immune system tissues or bodily fluids from an individual not having the immune system disorder. Thus, the invention provides a diagnostic method useful during diagnosis of an immune system disorder, which involves measuring the expression level of the gene encoding the TRID protein in immune system tissue or other cells or body fluid from an individual and comparing the measured gene expression level with a standard TRID gene expression level, whereby an increase or decrease in the gene expression level compared to the standard is indicative of an immune system disorder.

In particular, it is believed that certain tissues in mammals with cancer express significantly enhanced levels of the TRID protein and mRNA encoding the TRID when compared to a corresponding "standard" level. Further, it is believed that enhanced levels of the TRID protein can be detected in certain body fluids (e.g., sera and plasma) from mammals with such a cancer when compared to sera from mammals of the same species not having the cancer.

Thus, the invention provides a diagnostic method useful during diagnosis of an immune system disorder, including cancers which involves measuring the expression level of the gene encoding the TRID protein in immune system tissue or other cells or body fluid from an individual and comparing the measured gene expression level with a standard TRID gene expression level, whereby an increase or decrease in the gene expression level compared to the standard is indicative of an immune system disorder.

Where a diagnosis of a disorder in the immune system including diagnosis of a tumor has already been made according to conventional methods, the present invention is useful as a prognostic indicator, whereby patients exhibiting altered (particularly enhanced) gene expression will experience a worse clinical outcome relative to patients expressing the gene at a level nearer the standard level.

By "assaying the expression level of the gene encoding a TRID protein" is intended qualitatively or quantitatively measuring or estimating the level of TRID or the level of the mRNA encoding TRID in a first biological sample either directly (e.g., by determining or estimating absolute protein level or mRNA level) or relatively (e.g., by comparing to the TRID protein level or mRNA level in a second biological sample). Preferably, the TRID protein level or mRNA level in the first biological sample is measured or estimated and compared to a standard TRID protein level or mRNA level, the standard being taken from a second biological sample obtained from an individual not having the disorder or being determined by averaging levels from a population of individuals not having a disorder of the immune system. As will be appreciated in the art, once standard TRID protein levels or mRNA levels are known, they can be used repeatedly as a standard for comparison.

By "biological sample" is intended any biological sample obtained from an individual, body fluid, cell line, tissue culture, or other source which contains TRID protein or mRNA. As indicated, biological samples include body fluids (such as sera, plasma, urine, synovial fluid and spinal fluid) which contain free extracellular domain(s) (or soluble form (s)) of a TRID protein, immune system tissue, and other tissue sources found to express complete or extracellular domain of TRID. Methods for obtaining tissue biopsies and body fluids from mammals are well known in the art. Where the biological sample is to include mRNA, a tissue biopsy is the preferred source.

The invention also contemplates the use of a gene of the present invention for diagnosing mutations in the TRID gene. For example, if a mutation is present in one of the genes of the present invention, conditions would result from a lack of production of the receptor polypeptides of the present invention. Further, mutations which enhance receptor polypeptide activity would lead to diseases associated with an over expression of the receptor polypeptide, e.g., endotoxic shock. Mutations in the genes can be detected by comparing the sequence of the defective gene with that of a normal one. Subsequently one can verify that a mutant gene is associated with a disease condition or the susceptibility to a disease condition. That is, a mutant gene which leads to the overexpression of TRID would be associated with an inability of TRAIL to inhibit tumor growth.

Other immune system disorders which may be diagnosed by the foregoing assays include hypersensitivity, allergy, infectious disease, graft-host disease, immunodeficiency, autoimmune diseases and the like.

Individuals carrying mutations in the genes of the present invention may be detected at the DNA level by a variety of techniques. Nucleic acids used for diagnosis may be obtained from a patient's cells, such as from blood, urine, saliva and tissue biopsy among other tissues. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid of the instant invention can be used to identify and analyze mutations in the human genes of the present invention. For example, deletions and insertions can be detected by a change in the size of the amplified product in comparison to the normal genotype. Point mutations can be identified by hybridizing amplified DNA to radiolabeled RNA or alternatively, radio-labeled antisense DNA sequences of the present invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequencing primary used with double stranded PCR product or a single stranded template molecule generated by a modified PCR product. The sequence determination is performed by conventional procedures with radiolabeled nucleotides or by automatic sequencing procedures with fluorescent tags.

Sequence changes at the specific locations may be revealed by nuclease protection assays, such as RNase and S1 protection or the chemical cleavage method (for example, Cotton et al., PNAS, 85:4397–4401 (1985)).

Assaying TRID protein levels in a biological sample can occur using antibody-based techniques. For example, TRID protein expression in tissues can be studied with classical immunohistological methods (Jalkanen, M., et al., *J. Cell. Biol.* 101.976–985 (1985); Jalkanen, M., et al., *J. Cell. Biol.* 105:3087–3096 (1987)). Other antibody-based methods useful for detecting TRID gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying TRID protein levels in a biological sample obtained from an individual, TRID proteins can also be detected in vivo by imaging. Antibody labels or markers for in vivo imaging of TRID proteins include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A TRID-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TRID protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors: Gene Structure and Biological Activities," *Symp. Quant. Biol.* 51:597–609 (1986), Cold Spring Harbor; Beutler, B., and Cerami, A., *Annu. Rev. Biochem.* 57:505–518 (1988); Old, L. J., *Sci. Am.* 258:59–75 (1988); Fiers, W., *FEBS Lett.* 285:199–224 (1991)). The TNF-family ligands induce such various cellular responses by binding to TNF-family receptors. Cells which express a TRID polypeptide and have a potent cellular response to TNFR ligands include lymphocytes, endothelial cells, keratinocytes, and prostate tissue. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis.

Diseases associated with increased cell survival, or the inhibition of apoptosis, include cancers (such as follicular lymphomas, carcinomas with p53 mutations, and hormone-dependent tumors, such as breast cancer, prostate cancer, Kaposi's sarcoma and ovarian cancer); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Thus, in one aspect, the present invention is directed to a method for enhancing apoptosis induced by a TNF-family ligand, which involves administering to a cell which expresses a TNFR polypeptide an effective amount of an antagonist of the TRID polypeptide, capable of inhibiting TRID expression or its ligand binding ability (e.g., to TRAIL). Preferably, TNFR mediated signaling is increased to treat a disease wherein decreased apoptosis is exhibited. Antagonist can include monoclonal antibodies directed against the TRID polypeptide.

By "antagonist" is intended naturally occurring and synthetic compounds capable of enhancing or potentiating apoptosis. By "agonist" is intended naturally occurring and synthetic compounds capable of inhibiting apoptosis. Whether any candidate "antagonist" or "agonist" of the present invention can enhance or inhibit apoptosis can be determined using art-known TNF-family ligand/receptor cellular response assays, including those described in more detail below.

One such screening procedure involves the use of melanophores which are transfected to co-express a TNFR receptor which binds a TRAIL such as DR4 or DR5, described elsewhere herein, and the TRID receptor of the present invention. Such a screening technique is described in PCT WO 92/01810, published Feb. 6, 1992. Such an assay may be employed, for example, for screening for a compound which inhibits (or enhances) the activity of the receptor polypeptide of the present invention by contacting the melanophore cells which encode the receptors with both a TNF-family ligand and the candidate antagonist (or agonist). Inhibition or enhancement of the signal generated by the ligand indicates that the compound is an antagonist or agonist of TRID activity. The TRID polypeptide and its agonists inhibit activation of the TNFR receptor, e.g., TRAIL receptor, whereas antagonists will increase activation.

Other screening techniques include the use of cells which express a TRAIL receptor and TRID (for example, transfected CHO cells) in a system which measures extracellular pH changes caused by receptor activation, for example, as described in *Science* 246:181–296 (October 1989). For example, compounds may be contacted with a cell which expresses a TRAIL receptor polypeptide and TRID of the present invention and a second messenger response, e.g., signal transduction or pH changes, may be measured to determine whether the potential compound activates or inhibits the TRAIL receptor.

Another such screening technique involves introducing RNA encoding the receptors into Xenopus oocytes to transiently express TRID and a TRAIL receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing in cells a construct wherein the TRAIL receptor is linked to a phospholipase C or D. Such cells include endothelial cells, smooth muscle cells, embryonic kidney cells, etc. The screening may be accomplished as hereinabove described by detecting activation of the receptor or inhibition of activation of the receptor from the phospholipase signal in the presence of TRID either co-expressed or added in soluble form along with the candidate compound.

Another method involves screening for compounds which inhibit activation of a TRAIL receptor polypeptide in the presence of the TRID polypeptide of the present invention, either co-expressed or in soluble form. Agonists of the present invention are identified by determining inhibition of binding of labeled ligand to cells which have the TRAIL receptor on the surface thereof. Such a method involves transfecting a eukaryotic cell with DNA encoding a TRAIL binding receptor such that the cell expresses the receptor on its surface and contacting the cell with a compound in the presence of a labelled TRAIL and TRID. TRAIL can be labeled, e.g., by radioactivity. The amount of labeled TRAIL bound to the receptors is measured, e.g., by measuring radioactivity of the receptors. If the compound binds to the TRID receptor as determined by an increase of labeled TRAIL which binds to the TRAIL receptor, the compound is a TRID antagonist.

Further screening assays for agonist and antagonist of the present invention are described in Tartaglia, L. A., and Goeddel, D. V., *J. Biol. Chem.* 267(7):4304–4307(1992).

Thus, in a further aspect, a screening method is provided for determining whether a candidate TRID antagonist or agonist is capable of enhancing or inhibiting a cellular response to a TNF-family ligand (e.g., apoptosis induced by TRAIL). The method involves contacting cells which express a TNFR polypeptide with a candidate compound, TRID, and a TNF-family ligand, assaying a cellular response, and comparing the cellular response to a standard cellular response, the standard being assayed when contact is made with the ligand in the presence of TRID but in absence of the candidate compound, whereby an increased cellular response over the standard indicates that the candidate compound is an antagonist and a decreased cellular response compared to the standard indicates that the candidate compound is an agonist. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the TNFR polypeptide can be contacted with either an endogenous or exogenously administered TNF-family ligand.

Antagonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonist include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457–1458 (1995)). Further preferred antagonist includes polyclonal and monoclonal antibodies raised against the TRID polypeptide, or a fragment thereof.

Agonists according to the present invention include naturally occurring and synthetic compounds such as, for example, the CD40 ligand, neutral amino acids, zinc, estrogen, androgens, viral genes (such as Adenovirus E1B, Baculovirus p35 and IAP, Cowpox virus crmA, Epstein-Barr virus BHRF1, LMP-1, African swine fever virus LMW5-HL, and Herpesvirus ICP34.5), calpain inhibitors, cysteine protease inhibitors, and tumor promoters (such as PMA, Phenobarbital, and -Hexachlorocyclohexane). Other Agonists include polyclonal and monoclonal antagonist antibodies raised against TRAIL polypeptides or a fragment thereof.

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

Further agonist according to the present invention include soluble forms of TRID, i.e., TRID fragments that include the ligand binding domain from the extracellular region of the full-length receptor. Such soluble forms of the receptor, which may be naturally occurring or synthetic, antagonize TNFR mediated signaling by competing with the cell surface TNFR for binding to TNF-family ligands. Thus, soluble forms of the TRID receptor that include the ligand binding domain are novel cytokines capable of inhibiting apoptosis induced by TNF-family ligands. Other such cytokines are known in the art and include Fas B (a soluble form of the mouse Fas receptor) that acts physiologically to limit apoptosis induced by Fas ligand (Hughes, D. P. and Crispe, I. N., J. Exp. Med. 182:1395–1401(1995)).

As indicated polyclonal and monoclonal antibody agonist or antagonist according to the present invention can be raised according to the methods disclosed in Tartaglia, L. A., and Goeddel, D. V., J. Biol. Chem. 267(7):4304–4307 (1992); Tartaglia, L. A. et al., Cell 73:213–216 (1993), and PCT Application WO 94/09137. The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F (ab')$_2$ fragments lack the Fc fragment of intact antibody, clear more rapidly from the circulation, and may have less non-specific tissue binding of an intact antibody (Wahl et al., J. Nucl. Med. 24:316–325 (1983)).

Antibodies according to the present invention may be prepared by any of a variety of methods described above, and known in the art Proteins and other compounds which bind the extracellular domains are also candidate agonist and antagonist according to the present invention. Such binding compounds can be "captured" using the yeast two-hybrid system (Fields and Song, Nature 340:245–246 (1989)). A modified version of the yeast two-hybrid system has been described by Roger Brent and his colleagues (Gyuris, J. et al., Cell 75:791–803 (1993); Zervos, A. S. et al., Cell 72:223–232 (1993)).

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, TRID ligands, TRAIL, TNF-α, lymphotoxin-α (LT-α, also known as TNF-β), LT-β, FasL, CD40, CD27, CD30, 4-IBB, OX40 and nerve growth factor (NGF). Experiments concerning the ability of TRID to bind TRAIL are described below in Example 5.

Representative therapeutic applications of the present invention are discussed in-more detail below. The state of immunodeficiency that defines AIDS is secondary to a decrease in the number and function of CD4$^+$ T-lymphocytes. Recent reports estimate the daily loss of CD4$^+$ T cells to be between $3.5 \times 10^7$ and $2 \times 10^9$ cells (Wei X., et al., Nature 373:117–122 (1995)). One cause of CD4$^+$ T cell depletion in the setting of HIV infection is believed to be HIV-induced apoptosis. Indeed, HIV-induced apoptotic cell death has been demonstrated not only in vitro but also, more importantly, in infected individuals (Ameisen, J. C., AIDS 8:1197–1213 (1994); Finkel, T. H., and Banda, N. K., Curr. Opin. Immunol. 6:605–615(1995); Muro-Cacho, C. A. et al., J. Immunol. 154:5555–5566 (1995)). Furthermore, apoptosis and CD4$^+$ T-lymphocyte depletion is tightly correlated in different animal models of AIDS (Brunner, T., et al., Nature 373:441–444 (1995); Gougeon, M. L., et al., AIDS Res. Hum. Retroviruses 9:553–563 (1993)) and, apoptosis is not observed in those animal models in which viral replication does not result in AIDS (Gougeon, M. L. et al., AIDS Res. Hum. Retroviruses 9:553–563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al., J. Virol. 70:199–206(1996)). Further the TNF-family ligand was detectable in uninfected macrophages and its expression was upregulated following HIV infection resulting in selective killing of uninfected CD4 T-lymphocytes (Badley, A. D et al., J. Virol. 70:199–206(1996)). Thus, by the invention, a method for treating HIV$^+$ individuals is provided which involves administering soluble TRID (e.g., the extracellular domain) or an agonist of the present invention to reduce selective killing of CD4 T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Antagonist of the present invention are able to suppress the immune response to both allografts and xenografts because lymphocytes activated and differentiated into effector cells will express TNFR polypeptides, and thereby are susceptible to compounds which enhance TNFR activity. Thus, the present invention further provides a method for creating immune privileged tissues. Agonist of the invention can further be used in the treatment of Inflammatory Bowel-Disease.

Formulations

The TRID polypeptide composition will be formulated and dosed in a fashion consistent with good medical practice, taking into account the clinical condition of the individual patient (especially the side effects of treatment with TRID polypeptide alone), the site of delivery of the TRID polypeptide composition, the method of administration, the scheduling of administration, and other factors known to practitioners. The "effective amount" of TRID polypeptide for purposes herein is thus determined by such considerations.

As a general proposition, the total pharmaceutically effective amount of TRID polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TRID polypeptide is typically administered at a dose rate of about 1 µg/kg/hour to about 50 µg/kg/hour, either by 1–4 injections per day or by continuous subcutaneous infusions, for example, using amini-pump. An intravenous bag solution may also be employed. The length of treatment needed to observe changes and the interval following treatment for responses to occur appears to vary depending on the desired effect.

Pharmaceutical compositions containing the TRID of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The TRID polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Sustained-release TRID polypeptide compositions also include liposomally entrapped TRID polypeptides. Liposomes containing TRID polypeptides are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TNFR polypeptide therapy.

For parenteral administration, in one embodiment, the TRID polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the TRID polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The TRID polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of TRID polypeptide salts.

TRID polypeptides to be used for therapeutic administration must be sterile. Sterility is readily accomplished by filtration through sterile filtration membranes (e.g., 0.2 micron membranes). Therapeutic TRID polypeptide compositions generally are placed into a container having a sterile access port, for example, an intravenous solution bag or vial having a stopper pierceable by a hypodermic injection needle.

TRID polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous TRID polypeptide solution, and the resulting mixture is lyophilized. The infusion solution is prepared by reconstituting the lyophilized TRID polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNAs herein disclosed are used to clone genomic DNA of a TRID protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes. A Manual Of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man,* available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of the "His-tagged" Extracellular form of TRID in *E. coli*

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the amino terminus of that polypeptide.

The DNA sequence encoding the desired portion of the TRID protein comprising the extracellular form of the TRID amino acid sequence is amplified from the deposited cDNA clone using PCR oligonucleotide primers which anneal to sequence encoding the amino terminal sequences of the desired portion of the TRID protein and to carboxy terminal sequences of the desired portion of the extracellular form of the TRID protein in the deposited cDNA. Additional nucleotides containing restriction sites to facilitate cloning in the pQE9 vector are added to the 5' and 3' primer sequences, respectively.

For cloning the extracellular form of the TRID protein, the 5' primer has the sequence 5' CGC GGATCCACCACTGCCCGGCAGGAG 3' (SEQ ID NO:19) containing the underlined BamHI restriction site followed by 18 nucleotides of the amino terminal coding sequence of the extracellular TRID sequence in SEQ ID NO:2. One of ordinary skill in the art would appreciate, of course, that the point in the protein coding sequence where the 5' primer begins and where the 3' primer ends may be varied to amplify a DNA segment encoding any desired portion of the complete TRID protein shorter or longer than the extracellular form of the protein. The 3' primer has the sequence 5' GCG TCTAGACTAGTAATGAGAAGAGGCAGG 3' (SEQ ID NO:20) containing the underlined XbaI restriction site followed by 18 nucleotides complementary to the 3' end of cDNA encoding the extracellular domain of the TRID protein in SEQ ID NO:2.

The amplified TRID DNA fragment and the vector pQE9 are digested with BamHI and XbaI and the digested DNAs are then ligated together. Insertion of the TRID DNA into the restricted pQE9 vector places the TRID protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual,* 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing TRID protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the TRID is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the TRID is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

Example 2

Cloning and Expression of TRID in a Baculovirus Expression System

In this illustrative example, the plasmid shuttle vector pA2 is used to insert the cloned DNA encoding complete protein, including its naturally associated secretory signal (leader) sequence, into a baculovirus to express the mature TRID protein, using standard methods as described in Summers et al., *A Manual of Methods for Baculovirus Vectors and Insect Cell Culture Procedures,* Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the full length TRID protein in a deposited clone, including the AUG initiation codon and the naturally associated leader sequence shown in SEQ ID NO:2 is amplified using PCR oligonucleotide primers corresponding to the 5' and 3' sequences of the gene. The 5' primer for TRID has the sequence 5' CGC TCTAGACCGCCATCATGGCCCGGATCCCCAAG 3' (SEQ ID NO:21) containing the underlined XbaI restriction enzyme site. The described primers encode an efficient signal for initiation of translation in eukaryotic cells, as described by Kozak, M., *J. Mol. Biol.* 196:947–950 (1987). The 3 ' primer for TRID has the sequence 5' GCG TCTAGACTAGTAATGAGAAGAGGCAGG 3' (SEQ ID NO:22) containing the underlined XbaI restriction site.

The amplified fragment is isolated from a 1% agarose gel using a commercially available kit ("Geneclean," BIO 101 Inc., La Jolla, Calif.). The fragment then is digested with the appropriate restriction enzyme for each of the primers used, as specified above, and again is purified on a 1% agarose gel.

The plasmid is digested with the same restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and dephosphorylated plasmid are ligated together with T4 DNA ligase. *E. coli* HB101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human TNF receptor gene by digesting DNA from individual colonies using the enzymes used immediately above and then analyzing the digestion product by gel electrophoresis. The sequence of the cloned fragment is confirmed by DNA sequencing. This plasmid is designated herein pA2-TRID.

Five µg of the plasmid pA2-TRID is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413–7417 (1987). One µg of BaculoGold™ virus DNA and 5 µg of the plasmid pA2-TNFR are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days, the supernatant is collected and a plaque assay is performed, as described by Summers and Smith, supra. An agarose gel with "Bluo Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later, the supernatants of these culture dishes are harvested and then they are stored at 4° C. The recombinant virus is called V-TRID.

To verify the expression of the V-TRID, Sf9 cells are grown in Grace's medium supplemented with 10% heat-inactivated FBS. The cells are infected with the recombinant baculovirus V-TRID at a multiplicity of infection ("MOI") of about 2. If radiolabeled proteins are desired, 6 hours later the medium is removed and is replaced with SF900II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature protein and thus the cleavage point and length of the secretory signal peptide.

Example 3

Cloning and Expression of TRID in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include: human Hela 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The dihydrofolate reductase (DHFR) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pTRID-HA, is made by cloning a cDNA encoding TRID into the expression vector pcDNAI/Amp or pcDNAIII (which can be obtained from Invitrogen, Inc).

The expression vector pcDNAI/Amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the TRID is cloned into the polylinker region of the vector so that recombinant protein expression is directed by the CMV promoter. The plasmid construction strategy is as follows. The TRID cDNA of the deposited clone is amplified using primers that contain convenient restriction sites, much as described above for construction of vectors for expression of a TNF receptor in *E. coli*. Suitable primers include the following, which are used in this example. The 5' primer for TNFR-5, containing the underlined EcoRI site, has the following sequence: 5' CGCGAATTCCGCCATCATGGCCCGGATCCCCAAG 3' (SEQ ID NO:23). The 3' primer, containing the underlined XbaI site, has the following sequence: 5' GCG TCTAGAGTAATGAGAAGAGGCAGG 3' (SEQ ID NO:24).

The PCR amplified DNA fragment and the vector, pcDNAI/Amp, are digested with XbaI and EcoRI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the TRID polypeptide.

For expression of recombinant TRID, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TRID by the vector.

Expression of the pTRID-HA fusion protein is detected by radiolabeling and immunoprecipitation, using methods described in, for example Harlow et al., *Antibodies. A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer:150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of TRID polypeptides. Plasmid pC4 isaderivative of the plasmid pSV2-dhfr (ATCC Accession No.37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem.* et *Biophys. Acta,* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molecular and Cellular Biology* 5:438–447 (1985) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, XbaI, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the TRID receptor polypeptide in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes appropriate for the specific primers used to amplify TRID as outlined below and then dephosphorylated using calf intestinal phosphates by procedures known in the art. The vector is then isolated from a 1% agarose gel.

The DNA sequence encoding the TRID polypeptide is amplified using PCR oligonucleotide primers corresponding to the 5' and 3' sequences of the desired portion of the gene. The 5' primer for TRID containing the underlined XbaI site, has the following sequence: 5' CGC TCTAGACCGCCATCATGGCCCGGATCCCCAAG 3' (SEQ ID NO:25).

The 3' primer for TRID, containing the underlined XbaI site, has the following sequence:5' GCG TCTAGACTAGTAATGAGAAGAGGCAGG 3' (SEQ ID NO:26).

The amplified fragment is digested with the endonucleases which will cut at the engineered restriction site(s) and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days, single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Tissue distribution of TRID mRNA expression

Northern blot analysis was carried out to examine TRID gene expression in human tissues, using methods described by, among others, Sambrook et al., cited above. A cDNA probe containing the entire nucleotide sequence of the TRID protein (SEQ ID NO:1) was labeled with $^{32}$p using the rediprime™ DNA labeling system (Amersham Life Science), according to manufacturer's instructions. After labeling, the probe was purified using a CHROMA SPIN-100™ column (Clontech Laboratories, Inc.), according to manufacturer's protocol number PT1200-1. The purified labeled probe was then used to examine various human tissues for TRID mRNA.

Multiple Tissue Northern (MTN) blots containing various human tissues (H) or human immune system tissues (IM) were obtained from Clontech (Palo Alto, Calif.) and examined with labeled probe using ExpressHyb™ hybridization solution (Clontech) according to manufacturer's protocol number PT1190-1. Following hybridization and washing, the blots were mounted and exposed to film at −70° C. overnight. The films were developed according to standard procedures. Expression of TRID was detected in many normal human tissues, such as heart, brain, placenta, lung, liver, kidney, pancreas, spleen, thymus, peripheral blood leukocytes (PBLs), lymph node, bone marrow, and fetal liver, but not in most transformed cancer cell lines.

Expression of TRID was also assessed by Northern blot in the following cancer cell lines, HL60 (promyelocytic leukemia), Hela cell S3, K562 (chronic myelogeneous leukemia), MOLT4 (lymphoblast leukemia), Raji (Burkitt's lymphoma), SW480 (colorectal adenocarcinoma), A549 (lung carcinoma), and G361 (melanoma), and was detected in only SW480 and Hela cell S3.

Example 5

The Extracellular Domain of TRID Binds the Cytotoxic Ligand-TRAIL, Blocks TRAIL-Induced Apoptosis As discussed above, TRAIL/Apo2L is a cytotoxic ligand that belongs to the tumor necrosis factor (TNF) ligand family and induces rapid cell death of many transformed cell lines, but not normal tissues, despite its death domain containing receptor, DR4, being expressed on both cell types. This example identifies an antagonist decoy receptor, designated "TRAIL Receptor Without Intracellular Domain" or "TRID", that also binds TRAIL and may in part explain the resistant phenotype of normal tissues. That is, TRID, an antagonistic receptor, binds and sequesters TRAIL, but is incapable of transducing an intracellular signal.

Given the similarity of the extracellular ligand binding cysteine-rich domains of TRID and DR4, the present inventors theorized that TRID would also bind TRAIL. To confirm this, the soluble extracellular ligand binding domain of TRID was expressed as a fusion to the Fc portion of human immunoglobulin (IgG).

Figure 5A:
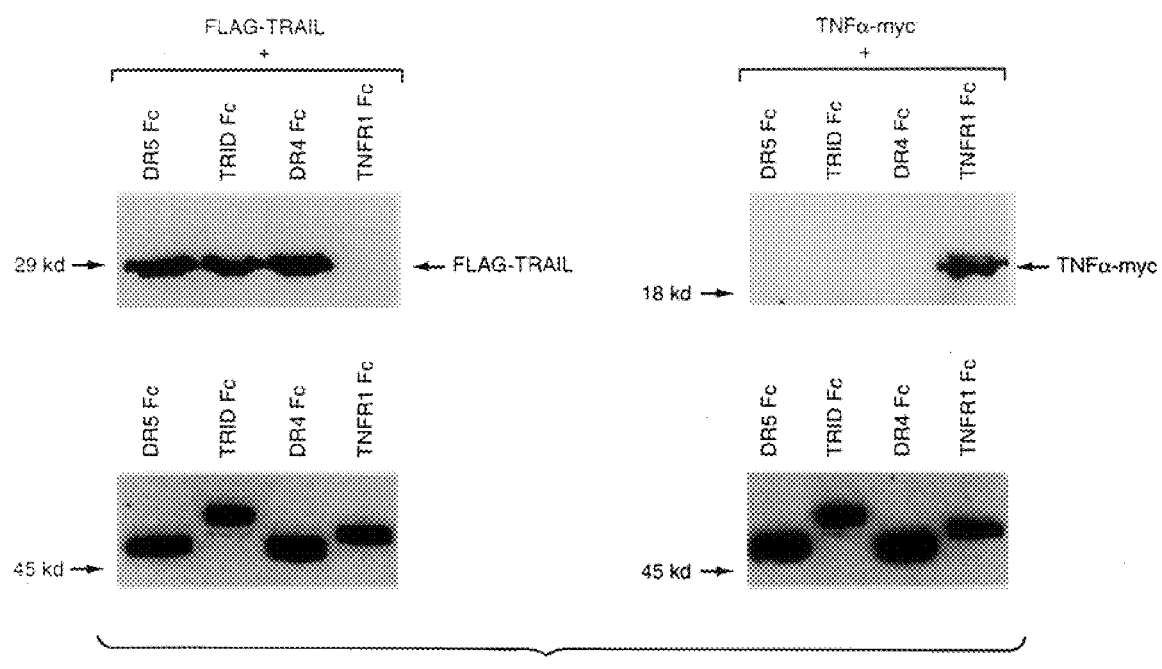
FIG. 5A is an immunoblot showing that TRID-Fc (as well as DR4 and DR5) specifically bound TRAIL, but not the related cytotoxic ligand TNFα. The bottom panel of FIG. 5A shows the input Fc-fusions present in the binding assays.

As shown in FIG. 5A, TRID-Fc specifically bound TRAIL, but not the related cytotoxic ligand TNFα. In this experiment, the Fc-extracellular domains of TRID, DR5, DR4, or TNFR1 and the corresponding ligands were prepared and binding assays performed as described in Pan et al., Science 276:111 (1997). The respective Fc-fusions were precipitated with protein G-Sepharose and co-precipitated soluble ligands were detected by immunoblotting with anti-Flag (Babco) or anti-myc-HRP (BMB). The bottom panel of FIG. 5A shows the input Fc-fusions present in the binding assays.

Figure 5B:
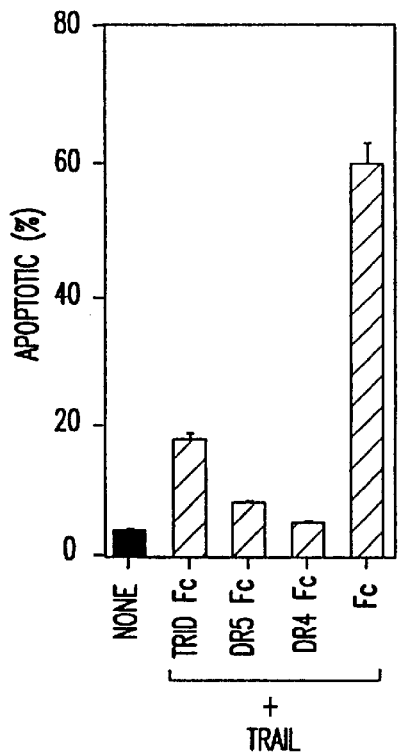
FIG. 5B is a bar graph showing that TRID-Fc blocked the ability of TRAIL to induce apoptosis. The data (mean±SD) shown in FIG. 5B are the percentage of apoptotic nuclei among total nuclei counted (n=4).

Additionally, TRID-Fc blocked the ability of TRAIL to induce apoptosis (FIG. 5B). MCF7 cells were treated with soluble TRAIL (200 ng/ml) in the presence of equal amounts of Fc-fusions or Fc alone. Six hours later, cells were fixed and examined as desribed in Pan et al., Id. The data (mean±SD) shown in FIG. 5B are the percentage of apoptotic nuclei among total nuclei counted (n=4).

Figure 5C:
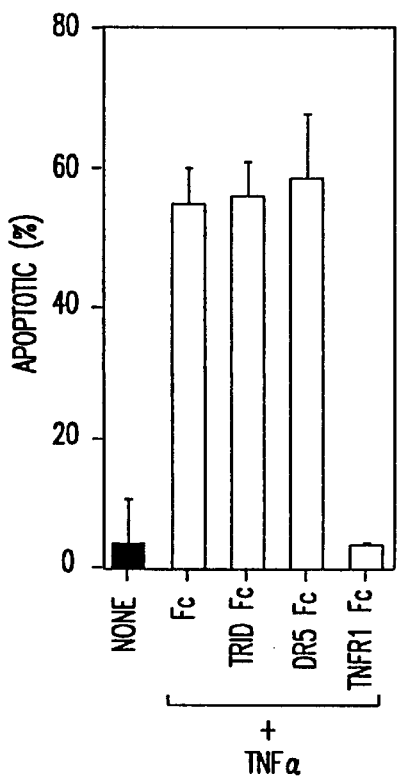
FIG. 5C is a bar graph showing that TRID-Fc had no effect on TNFα-induced apoptosis under conditions where TNFR1-Fc completely abolished TNFα killing.

Further, TRID-Fc had no effect on TNFα-induced apoptosis under conditions where TNFR1-Fc completely abolished TNFα killing (FIG. 5C). MCF7 cells were treated with TNFα (40 ng/ml; Genentech, Inc.) in the presence of equal amounts of Fc-fusions or Fc alone. Nuclei were stained and examined 11–15 hours later.

Example 6

TRID Protects Cells from TRAIL-Induced Apoptosis

Figure 6:
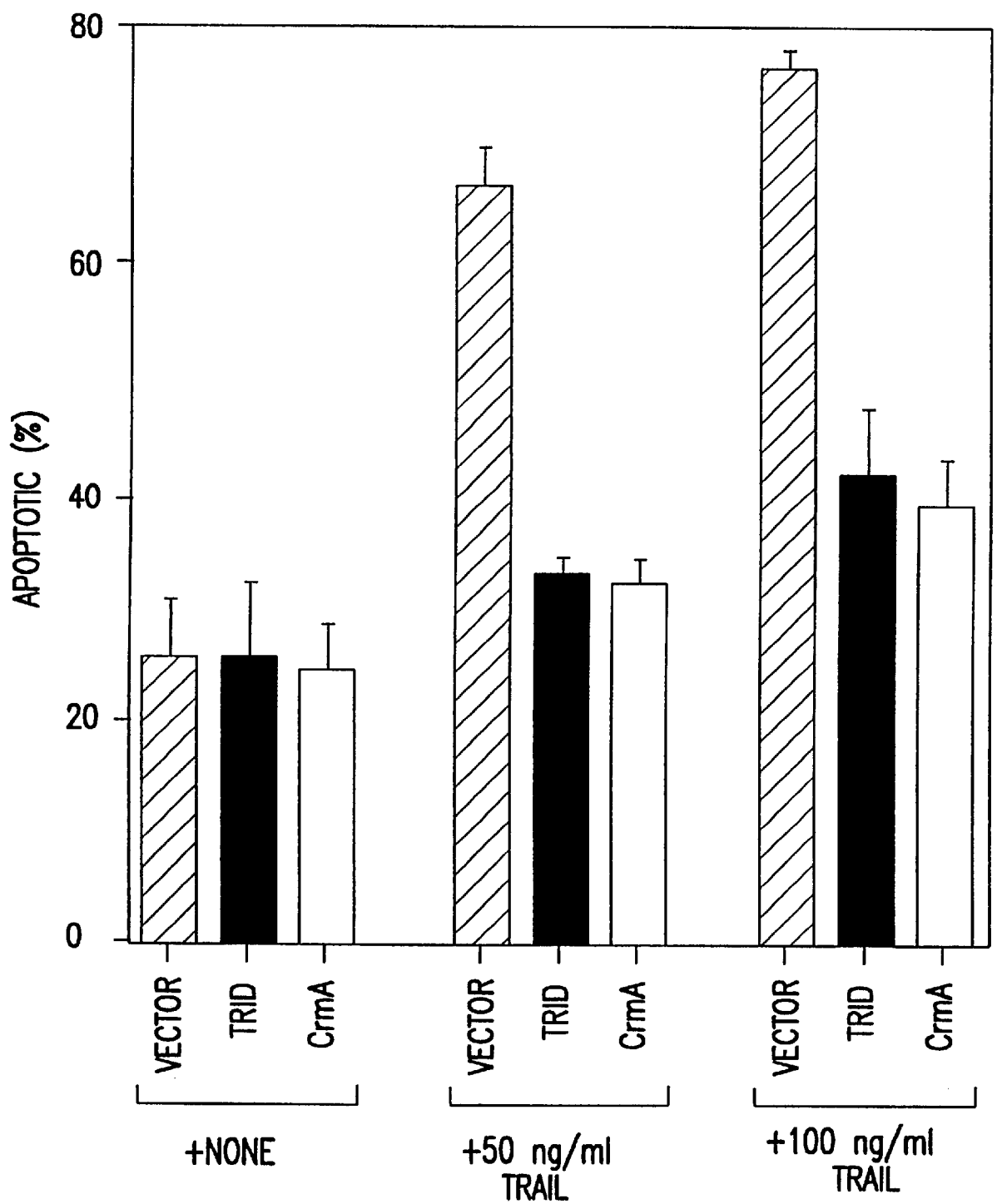
FIG. 6 is a bar graph showing that MCF7 cells expressing TRID were protected from TRAIL-induced apoptosis, as were cells expressing the virally encoded caspase inhibitor CrmA.

As shown in FIG. 6, cells expressing TRID were protected from TRAIL-induced apoptosis as were cells expressing the virally encoded caspase inhibitor CrmA.

Given the absence of an intracellular signalling domain, it was likely that native TRID could itself similarly attenuate TRAIL-induced cell death. This was confirmed by asking if overexpression of native TRID in TRAIL-sensitive cells (MCF7) would protect them from TRAIL-induced apoptosis. Overexpression of TRID by itself did not induce apoptosis. However, when the cells were exposed to TRAIL, cells expressing TRID were as protected from TRAIL-induced apoptosis as were cells expressing the virally encoded caspase inhibitor CrmA (FIG. 6).

MCF7 cells were transfected with TRID, or CrmA expression construct or vector alone together with a b-Gal reporter construct. Twenty four hours after transfection, TRAIL was added at 50 ng/ml and 100 ng/ml. Six hours later, cells were stained with X-gal as previously described (A. M. Chinnaiyan, et al., Cell 81, 505–12 (1995); M. P. Boldin, et al., J Biol Chem 270, 7795–8 (1995); F. C. Kischkel, et al., EMBO 14, 5579–5588 (1995)), and examined microscopically.

Taken together, these findings are consistent with a guardian role for TRID that allows normal tissues to withstand the potentially deleterious effects of constitutively expressed TRAIL.

The new identification of the antagonist decoy receptor TRID as a receptor for TRAIL adds further complexity to the biology of TRAIL-initiated signal transduction.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated nucleic acid molecule comprising a first polynucleotide sequence 95% or more identical to a second polynucleotide sequence selected from the group consisting of:
   (a) a polynucleotide sequence encoding amino acids −26 to 233 of SEQ ID NO:2;
   (b) a polynucleotide sequence encoding amino acids −25 to 233 of SEQ ID NO:2;
   (c) a polynucleotide sequence encoding amino acids 1 to 233 of SEQ ID NO:2; and
   (d) a polynucleotide sequence complementary to any of the polynucleotide sequences in (a), (b) or (c) above;
   wherein percentage identity is determined using the BESTFIT program with parameters that calculate identity over the full length of the second polynucleotide sequence and that allows gaps of up to 5% of the total number of nucleotides of said nucleotide sequence.

2. The isolated nucleic acid molecule of claim 1 wherein said second polynucleotide sequence is (a).

3. The isolated nucleic acid molecule of claim 1 which comprises polynucleotide sequence (a).

4. The isolated nucleic acid molecule of claim 1 wherein said second polynucleotide sequence is (b).

5. The isolated nucleic acid molecule of claim 1 which comprises polynucleotide sequence (b).

6. The isolated nucleic acid molecule of claim 1 wherein said second polynucleotide sequence is (c).

7. The isolated nucleic acid molecule of claim 1 which comprises polynucleotide sequence (c).

8. The isolated nucleic acid molecule of claim 1 wherein said second polynucleotide sequence comprises nucleotides 261 to 959 of SEQ ID NO:1.

9. The isolated nucleic acid molecule of claim 1 wherein said second polynucleotide sequence is (d).

10. The isolated nucleic acid molecule of claim 1 which comprises polynucleotide sequence (d).

11. The isolated nucleic acid molecule of claim 1 wherein said nucleic acid molecule comprises a heterologous polynucleotide sequence.

12. The isolated nucleic acid molecule of claim 11 wherein said heterologous polynucleotide sequence encodes a polypeptide.

13. The isolated nucleic acid molecule of claim 12 wherein said heterologous polynucleotide sequence encodes an Fc polypeptide.

14. A method for making a recombinant vector comprising inserting the isolated nucleic acid molecule of claim 1 into a vector.

15. A recombinant vector comprising the isolated nucleic acid molecule of claim 1.

16. The recombinant vector of claim 15 wherein said nucleic acid molecule is operably associated with a heterologous regulatory sequence that controls gene expression.

17. A recombinant host cell comprising the isolated nucleic acid molecule of claim 1.

18. The recombinant host cell of claim 17 wherein said nucleic acid molecule is operably associated with a heterologous regulatory sequence that controls gene expression.

19. The isolated nucleic acid of claim 1 wherein said second polynucleotide sequence is selected from the group consisting of (a), (b), and (c), and wherein said first polynucleotide sequence encodes a polypeptide.

20. A method for producing a polypeptide, comprising:
(a) culturing a host cell comprising the nucleic acid molecule of claim 19 under conditions suitable to produce the polypeptide encoded by said nucleic acid; and
(b) recovering said polypeptide.

21. An isolated nucleic acid molecule comprising a first polynucleotide sequence 95% or more identical to a second polynucleotide sequence selected from the group consisting of:
(a) a polynucleotide sequence encoding a TRID (TRAIL receptor without intracellular domain) polypeptide having the complete amino acid sequence encoded by the cDNA clone contained in ATCC Deposit No. 97798;
(b) a polynucleotide sequence encoding the mature TRID polypeptide encoded by the cDNA clone contained in ATCC Deposit No. 97798; and
(c) a polynucleotide sequence complementary to any of the polynucleotide sequences in (a) or (b) above;
wherein percentage identity is determined using the BESTFIT program with parameters that calculate identity over the full length of the second polynucleotide sequence and that allows gaps of up to 5% of the total number of nucleotides of said nucleotide sequence.

22. The isolated nucleic acid molecule of claim 21 wherein said second polynucleotide sequence is (a).

23. The isolated nucleic acid molecule of claim 21 which comprises polynucleotide sequence (a).

24. The isolated nucleic acid molecule of claim 21 wherein said second polynucleotide sequence is (b).

25. The isolated nucleic acid molecule of claim 21 which comprises polynucleotide sequence (b).

26. The isolated nucleic acid molecule of claim 21 wherein said second polynucleotide sequence is (c).

27. The isolated nucleic acid molecule of claim 21 which comprises polynucleotide sequence (c).

28. The isolated nucleic acid molecule of claim 21 wherein said nucleic acid molecule comprises a heterologous polynucleotide sequence.

29. The isolated nucleic acid molecule of claim 28 wherein said heterologous polynucleotide sequence encodes a polypeptide.

30. The isolated nucleic acid molecule of claim 29 wherein said heterologous polynucleotide sequence encodes an Fc polypeptide.

31. A method for making a recombinant vector comprising inserting the isolated nucleic acid molecule of claim 21 into a vector.

32. A recombinant vector comprising the isolated nucleic acid molecule of claim 21.

33. The recombinant vector of claim 32 wherein said nucleic acid molecule is operably associated with a heterologous regulatory sequence that controls gene expression.

34. A recombinant host cell comprising the isolated nucleic acid molecule of claim 21.

35. The recombinant host cell of claim 34 wherein said nucleic acid molecule is operably associated with a heterologous regulatory sequence that controls gene expression.

36. The isolated nucleic acid of claim 21, wherein said second polynucleotide sequence is selected from the group consisting of (a) and (b), and wherein said first polynucleotide sequence encodes a polypeptide.

37. A method for producing a polypeptide, comprising:
(a) culturing a host cell comprising the nucleic acid molecule of claim 36 under conditions suitable to produce the polypeptide encoded by said nucleic acid; and
(b) recovering said polypeptide.

38. An isolated nucleic acid molecule comprising a first polynucleotide sequence 95% or more identical to a second polynucleotide sequence selected from the group consisting of:
(a) a polynucleotide sequence encoding a polypeptide comprising the amino acid sequence of residues m to 233 of SEQ ID NO:2, where m is an integer in the range of −26 to 27;
(b) a polynucleotide sequence encoding a polypeptide comprising the amino acid sequence of residues −26 to x of SEQ ID NO:2, where x is an integer in the range of 123 to 233; and
(c) a polynucleotide sequence encoding a polypeptide having the amino acid sequence consisting of residues m to x of SEQ ID NO2, m and x are defined in (a) and (b) above;
wherein percentage identity is determined using the BESTFIT program with parameters that calculate identity over the full length of the second polynucleotide sequence and that allows gaps of up to 5% of the total number of nucleotides of said nucleotide sequence.

39. The isolated nucleic acid molecule of claim 38 wherein said second polynucleotide sequence is (a).

40. The isolated nucleic acid molecule of claim 38 which comprises polynucleotide sequence (a).

41. The isolated nucleic acid molecule of claim 40 which comprises a polynucleotide sequence encoding amino acids 27 to 233 of SEQ ID NO:2.

42. The isolated nucleic acid molecule of claim 38 wherein said second polynucleotide sequence is (b).

43. The isolated nucleic acid molecule of claim 38 which comprises polynucleotide sequence (b).

44. The isolated nucleic acid molecule of claim 38 wherein said second polynucleotide sequence is (c).

45. The isolated nucleic acid molecule of claim 38 which comprises polynucleotide sequence (c).

46. The isolated nucleic acid molecule of claim 38 wherein said nucleic acid molecule comprises a heterologous polynucleotide sequence.

47. The isolated nucleic acid molecule of claim 46 wherein said heterologous polynucleotide sequence encodes a polypeptide.

48. The isolated nucleic acid molecule of claim 47 wherein said heterologous polynucleotide sequence encodes an Fc polypeptide.

49. A method for making a recombinant vector comprising inserting the isolated nucleic acid molecule of claim 38 into a vector.

50. A recombinant vector comprising the isolated nucleic acid molecule of claim 38.

51. The recombinant vector of claim 50 wherein said nucleic acid molecule is operably associated with a heterologous regulatory sequence that controls gene expression.

52. A recombinant host cell comprising the isolated nucleic acid molecule of claim 38.

53. The recombinant host cell of claim 52 wherein said nucleic acid molecule is operably associated with a heterologous regulatory sequence that controls gene expression.

54. A method for producing a polypeptide, comprising:
  (a) culturing a host cell comprising the nucleic acid molecule of claim 38 under conditions suitable to produce the polypeptide encoded by said nucleic acid; and
  (b) recovering said polypeptide.

55. An isolated nucleic acid molecule encoding a fragment of amino acids 26 to 233 of SEQ ID NO:2, wherein said fragment binds an antibody specific to the polypeptide having amino acids 1 to 214 of SEQ ID NO:2.

56. The isolated nucleic acid molecule of claim 55 wherein said nucleic acid molecule comprises a heterologous polynucleotide sequence.

57. The isolated nucleic acid molecule of claim 56 wherein said heterologous polynucleotide sequence encodes a polypeptide.

58. The isolated nucleic acid molecule of claim 57 wherein said heterologous polynucleotide sequence encodes an Fc polypeptide.

59. A method for making a recombinant vector comprising inserting the isolated nucleic acid molecule of claim 55 into a vector.

60. A recombinant vector comprising the isolated nucleic acid molecule of claim 55.

61. The recombinant vector of claim 60 wherein said nucleic acid molecule is operably associated with a heterologous regulatory sequence that controls gene expression.

62. A recombinant host cell comprising the isolated nucleic acid molecule of claim 55.

63. The recombinant host cell of claim 62 wherein said nucleic acid molecule is operably associated with a heterologous regulatory sequence that controls gene expression.

64. A method for producing a polypeptide, comprising:
  (a) culturing a host cell comprising the nucleic acid molecule of claim 55 under conditions suitable to produce the polypeptide encoded by said nucleic acid; and
  (b) recovering said polypeptide.

65. An isolated nucleic acid encoding a polypeptide comprising 30 contiguous amino acids from amino acids 1 to 233 of SEQ ID NO:2.

66. The isolated nucleic acid of claim 65 which encodes a polypeptide comprising amino acids 1 to 214 of SEQ ID NO:2.

67. The isolated nucleic acid of claim 65 which encodes a polypeptide comprising amino acids 215 to 233 of SEQ ID NO:2.

68. The isolated nucleic acid of claim 65 which encodes a polypeptide comprising 50 contiguous amino acids from amino acids 1 to 233 of SEQ ID NO:2.

69. The isolated nucleic acid molecule of claim 65 wherein said nucleic acid molecule comprises a heterologous polynucleotide sequence.

70. The isolated nucleic acid molecule of claim 69 wherein said heterologous polynucleotide sequence encodes a polypeptide.

71. The isolated nucleic acid molecule of claim 70 wherein said heterologous polynucleotide sequence encodes an Fc polypeptide.

72. A method for making a recombinant vector comprising inserting the isolated nucleic acid molecule of claim 65 into a vector.

73. A recombinant vector comprising the isolated nucleic acid molecule of claim 65.

74. The recombinant vector of claim 73 wherein said nucleic acid molecule is operably associated with a heterologous regulatory sequence that controls gene expression.

75. A recombinant host cell comprising the isolated nucleic acid molecule of claim 65.

76. The recombinant host cell of claim 75 wherein said nucleic acid molecule is operably associated with a heterologous regulatory sequence that controls gene expression.

77. A method for producing a polypeptide, comprising:
  (a) culturing a host cell comprising the nucleic acid molecule of claim 65 under conditions suitable to produce the polypeptide encoded by said nucleic acid; and
  (b) recovering said polypeptide.

78. An isolated nucleic acid molecule comprising a polynucleotide sequence selected from the group consisting of:
  (a) a polynucleotide sequence encoding from amino acids 42 to 50 of SEQ ID NO:2;
  (b) a polynucleotide sequence encoding from amino acids 53 to 59 of SEQ ID NO:2;
  (c) a polynucleotide sequence encoding from amino acids 65 to 76 of SEQ ID NO:2;
  (d) a polynucleotide sequence encoding from amino acids 84 to 96 of SEQ ID NO:2;
  (e) a polynucleotide sequence encoding from amino acids 100 to 110 of SEQ ID NO:2; and
  (f) a polynucleotide sequence encoding from amino acids 116 to 122 of SEQ ID NO:2.

79. The isolated nucleic acid molecule of claim 78 wherein said polynucleotide sequence is (a).

80. The isolated nucleic acid molecule of claim 79 wherein said polynucleotide sequence is nucleotides 384 to 410 of SEQ ID NO:1.

81. The isolated nucleic acid molecule of claim 78 wherein said polynucleotide sequence is (b).

82. The isolated nucleic acid molecule of claim 81 wherein said polynucleotide sequence is nucleotides 417 to 437 of SEQ ID NO:1.

83. The isolated nucleic acid molecule of claim 78 wherein said polynucleotide sequence is (c).

84. The isolated nucleic acid molecule of claim 83 wherein said polynucleotide sequence is nucleotides 453 to 488 of SEQ ID NO:1.

85. The isolated nucleic acid molecule of claim 78 wherein said polynucleotide sequence is (d).

86. The isolated nucleic acid molecule of claim 85 wherein said polynucleotide sequence is nucleotides 510 to 548 of SEQ ID NO:1.

87. The isolated nucleic acid molecule of claim 78 wherein said polynucleotide sequence is (e).

88. The isolated nucleic acid molecule of claim 87 wherein said polynucleotide sequence is nucleotides 558 to 590 of SEQ ID NO:1.

89. The isolated nucleic acid molecule of claim 78 wherein said polynucleotide sequence is (f).

90. The isolated nucleic acid molecule of claim 89 wherein said polynucleotide sequence is nucleotides 606 to 626 of SEQ ID NO:1.

91. The isolated nucleic acid molecule of claim 78 wherein said nucleic acid molecule comprises a heterologous polynucleotide sequence.

92. The isolate nucleic acid molecule of claim 91 wherein said heterologous polynucleotide sequence encodes a polypeptide.

93. The isolated nucleic acid molecule of claim 92 wherein said heterologous polynucleotide sequence encodes an Fc polypeptide.

94. A method for making a recombinant vector comprising inserting the isolated nucleic acid molecule of claim 78 into a vector.

95. A recombinant vector comprising the isolated nucleic acid molecule of claim 78.

96. The recombinant vector of claim 95 wherein said nucleic acid molecule is operably associated with a heterologous regulatory sequence that controls gene expression.

97. A recombinant host cell comprising the isolated nucleic acid molecule of claim 78.

98. The recombinant host cell of claim 97, wherein said nucleic acid molecule is operably associated with a heterologous regulatory sequence that controls gene expression.

99. A method for a polypeptide, comprising:
  (a) culturing a host cell comprising the nucleic acid molecule of claim 78 under conditions suitable to produce the polypeptide encoded by said nucleic acid; and
  (b) recovering said polypeptide.

100. An isolated nucleic acid molecule comprising a first polynucleotide sequence which hybridizes at 42° C. in a solution in a hybridization buffer consisting of 50% formamide, 5×SSC, 50 mM sodium phosphate (pH 7.6), 5×Denhardt's solution, 10% dextran sulfate, and 20 µg/ml denatured, sheared salmon sperm DNA, followed by washing in 0.1×SSC at 65° C., to the complementary sequence of a second polynucleotide sequence selected from the group consisting of:
  (a) nucleotides 384 to 410 of SEQ ID NO:1;
  (b) nucleotides 417 to 437 of SEQ ID NO:1;
  (c) nucleotides 453 to 488 of SEQ ID NO:1;
  (d) nucleotides 510 to 548 of SEQ ID NO:1;
  (e) nucleotides 558 to 590 of SEQ ID NO:1; and
  (f) nucleotides 606 to 626 of SEQ ID NO:1.

101. The isolated nucleic acid molecule of claim 100 wherein said second polynucleotide sequence is (a).

102. The isolated nucleic acid molecule of claim 100 wherein said second polynucleotide sequence is (b).

103. The isolated nucleic acid molecule of claim 100 wherein said second polynucleotide sequence is (c).

104. The isolated nucleic acid molecule of claim 100 wherein said second polynucleotide sequence is (d).

105. The isolated nucleic acid molecule of claim 100 wherein said second polynucleotide sequence is (e).

106. The isolated nucleic acid molecule of claim 100 wherein said second polynucleotide sequence is (f).

107. The isolated nucleic acid molecule of claim 100 which encodes a polypeptide that binds an antibody specific to the polypeptide having amino acids −26 to 233 of SEQ ID NO:2.

108. The isolated nucleic acid molecule of claim 100 wherein said nucleic acid molecule comprises a heterologous polynucleotide sequence.

109. The isolated nucleic acid molecule of claim 108 wherein said heterologous polynucleotide sequence encodes a polypeptide.

110. The isolated nucleic acid molecule of claim 109 wherein said heterologous polynucleotide sequence encodes an Fc polypeptide.

111. A method for making a recombinant vector comprising inserting the isolated nucleic acid molecule of claim 100 into a vector.

112. A recombinant vector comprising the isolated nucleic acid molecule of claim 100.

113. The recombinant vector of claim 112 wherein said nucleic acid molecule is operably associated with a heterologous regulatory sequence that controls gene expression.

114. A recombinant host cell comprising the isolated nucleic acid molecule of claim 100.

115. The recombinant host cell of claim 114 wherein said nucleic acid molecule is operably associated with a heterologous regulatory sequence that controls gene expression.

116. A method for producing a polypeptide, comprising:
  (a) culturing a host cell comprising the nucleic acid molecule of claim 100 under conditions suitable to produce the polypeptide encoded by said nucleic acid; and
  (b) recovering said polypeptide.

117. An isolated nucleic acid comprising a first polynucleotide sequence 90% or more identical to a second polynucleotide sequence selected from the group consisting of:
  (a) a polynucleotide sequence encoding amino acids −26 to 233 of SEQ ID NO:2;
  (b) a polynucleotide sequence encoding amino acids −25 to 233 SEQ ID NO2;
  (c) a polynucleotide sequence encoding amino acids 1 to 233 SEQ ID NO2; and
  (d) a polynucleotide sequence complementary to any of the polynucleotide sequences in (a), (b) or (c) above;
  wherein percentage identity is determined using the BESTFIT program with parameters that calculate identity over the full length of the second polynucleotide sequence and that allows gaps of up to 10% of the total number of nucleotides of said nucleotide sequence.

118. The isolated nucleic acid molecule of claim 117 wherein said second polynucleotide sequence is (a).

119. The isolated nucleic acid molecule of claim 117 which comprises polynucleotide sequence (a).

120. The isolated nucleic acid molecule of claim 117 wherein said second polynucleotide sequence is (b).

121. The isolated nucleic acid molecule of claim 117 which comprises polynucleotide sequence (b).

122. The isolated nucleic acid molecule of claim 117 wherein said second polynucleotide sequence is (c).

123. The isolated nucleic acid molecule of claim 117 which comprises polynucleotide sequence (c).

124. The isolated nucleic acid molecule of claim 123 wherein said second polynucleotide sequence comprises nucleotide 261 to 959 of SEQ ID NO:1.

125. The isolated nucleic acid molecule of claim 117 wherein said second polynucleotide sequence is (d).

126. The isolated nucleic acid molecule of claim 117 which comprises polynucleotide sequence (d).

127. The isolated nucleic acid molecule of claim 117 wherein said nucleic acid molecule comprises a heterologous polynucleotide sequence.

128. The isolated nucleic acid molecule of claim 127 wherein said heterologous polynucleotide sequence encodes a polypeptide.

129. The isolated nucleic acid molecule of claim 128 wherein said heterologous polynucleotide sequence encodes an Fc polypeptide.

130. A method for making a recombinant vector comprising inserting the isolated nucleic acid molecule of claim 117 into a vector.

131. A recombinant vector comprising the isolated nucleic acid molecule of claim 117.

132. The recombinant vector of claim 131 wherein said nucleic acid molecule is operably associated with a heterologous regulatory sequence that controls gene expression.

133. A recombinant host cell comprising the isolated nucleic acid molecule of claim 117.

134. The recombinant host cell of claim 133 wherein said nucleic acid molecule is operably associated with a heterologous regulatory sequence that controls gene expression.

135. The isolated nucleic acid of claim 117 wherein said second polynucleotide sequence is selected from the group consisting of (a), (b), and (c), and wherein said first polynucleotide sequence encodes a polypeptide.

136. A method for producing a polypeptide, comprising:
(a) culturing a host cell comprising the nucleic acid molecule of claim 135 under conditions suitable to produce the polypeptide encoded by said nucleic acid; and
(b) recovering said polypeptide.

137. An isolated nucleic acid molecule comprising a first polynucleotide sequence 90% or more identical to a second polynucleotide sequence selected from the group consisting of:
(a) a polynucleotide sequence encoding a TRID (TRAIL receptor without intracellular domain) polypeptide having the complete amino acid sequence encoded by the cDNA clone contained in ATCC Deposit No. 97798;
(b) a polynucleotide sequence encoding the mature TRID polypeptide encoded by the cDNA clone contained in ATCC Deposit No. 97798; and
(c) a polynucleotide sequence complementary to any of the polynucleotide sequences in (a) or (b) above;
wherein percentage identity is determined using the BESTFIT program with parameters that calculate identity over the full length of the second polynucleotide sequence and that allows gaps of up to 10% of the total number of nucleotides of said nucleotide sequence.

138. The isolated nucleic acid molecule of claim 137 wherein said second polynucleotide sequence is (a).

139. The isolated nucleic acid molecule of claim 137 which comprises polynucleotide sequence (a).

140. The isolated nucleic acid molecule of claim 137 wherein said second polynucleotide sequence is (b).

141. The isolated nucleic acid molecule of claim 137 which comprises polynucleotide sequence (b).

142. The isolated nucleic acid molecule of claim 137 wherein said second polynucleotide sequence is (c).

143. The isolated nucleic acid molecule of claim 137 which comprises polynucleotide sequence (c).

144. The isolated nucleic acid molecule of claim 137 wherein said nucleic acid molecule comprises a heterologous polynucleotide sequence.

145. The isolated nucleic acid molecule of claim 144 wherein said heterologous polynucleotide sequence encodes a polypeptide.

146. The isolated nucleic acid molecule of claim 145 wherein said heterologous polynucleotide sequence encodes an Fc polypeptide.

147. A method for making a recombinant vector comprising inserting the isolated nucleic acid molecule of claim 137 into a vector.

148. A recombinant vector comprising the isolated nucleic acid molecule of claim 137.

149. The recombinant vector of claim 148 wherein said nucleic acid molecule is operably associated with a heterologous regulatory sequence that controls gene expression.

150. A recombinant host cell comprising the isolated nucleic acid molecule of claim 137.

151. The recombinant host cell of claim 150 wherein said nucleic acid molecule is operably associated with a heterologous regulatory sequence that controls gene expression.

152. The isolated nucleic acid molecule of claim 137 wherein said second polynucleotide sequence is selected from the group consisting of (a) and (b), and wherein said first polynucleotide sequence encodes a polypeptide.

153. A method for producing a polypeptide, comprising:
(a) culturing a host cell comprising the nucleic acid molecule of claim 152 under conditions suitable to produce the polypeptide encoded by said nucleic acid; and
(b) recovering said polypeptide.

* * * * *

UNITED STATES PATENT AND TRADEMARK OFFICE
CERTIFICATE OF CORRECTION

PATENT NO.    : 6,261,801 B1
DATED         : July 17, 2001
INVENTOR(S)   : Wei et al.

It is certified that error appears in the above-identified patent and that said Letters Patent is hereby corrected as shown below:

<u>Title page,</u>
Item [73], please remove "Sceineces," and insert therein -- Sciences --.

Signed and Sealed this

Nineteenth Day of August, 2003

JAMES E. ROGAN
*Director of the United States Patent and Trademark Office*